(12) United States Patent
Nedivi

(10) Patent No.: US 7,884,078 B2
(45) Date of Patent: Feb. 8, 2011

(54) CPG15 COMPOUNDS AS INSULIN RECEPTOR AND INSULIN-LIKE GROWTH FACTOR RECEPTOR AGONISTS

(75) Inventor: Elly Nedivi, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/704,823

(22) Filed: Feb. 9, 2007

(65) Prior Publication Data
US 2007/0299010 A1 Dec. 27, 2007

Related U.S. Application Data

(60) Provisional application No. 60/772,450, filed on Feb. 10, 2006.

(51) Int. Cl.
A61K 38/30 (2006.01)
A61K 38/28 (2006.01)
G01N 33/567 (2006.01)
C12P 21/00 (2006.01)
A61K 38/16 (2006.01)

(52) U.S. Cl. ............... 514/18.9; 514/5.9; 435/7.21; 435/69.1; 530/324

(58) Field of Classification Search ............ None
See application file for complete search history.

(56) References Cited

U.S. PATENT DOCUMENTS

| | | |
|---|---|---|
| 4,892,538 A | 1/1990 | Aebischer et al. |
| 5,011,472 A | 4/1991 | Aebischer et al. |
| 5,106,627 A | 4/1992 | Aebischer et al. |
| 5,399,346 A | 3/1995 | Anderson et al. |
| 5,817,784 A | 10/1998 | Theill et al. |
| 5,859,197 A | 1/1999 | Theill et al. |
| 6,042,579 A | 3/2000 | Elsberry et al. |
| 6,174,869 B1 | 1/2001 | Barrett |
| 6,379,882 B1 | 4/2002 | Bitler et al. |
| 6,528,479 B1 | 3/2003 | Tanaka et al. |
| 6,582,960 B1 | 6/2003 | Martin et al. |
| 6,875,741 B2 | 4/2005 | Pillutla et al. |
| RE38,915 E | 12/2005 | Sportsman et al. |
| 7,115,415 B2 | 10/2006 | Goddard et al. |
| 7,129,324 B2 | 10/2006 | Goddard et al. |
| 2002/0192209 A1 | 12/2002 | Baker et al. |
| 2003/0036635 A1 | 2/2003 | Baker et al. |
| 2003/0114407 A1 | 6/2003 | Monia et al. |
| 2003/0114412 A1 | 6/2003 | Ward et al. |
| 2004/0023386 A1 | 2/2004 | King |
| 2004/0176291 A1 | 9/2004 | Nedivi et al. |
| 2005/0187175 A1 | 8/2005 | Nedivi et al. |
| 2005/0281812 A1 | 12/2005 | Cohen et al. |
| 2008/0125388 A1 | 5/2008 | Nedivi et al. |
| 2008/0227745 A1 | 9/2008 | Nedivi et al. |

FOREIGN PATENT DOCUMENTS

| | | |
|---|---|---|
| WO | WO 00/73348 A2 | 12/2000 |
| WO | WO 01/53312 | 7/2001 |
| WO | WO 01/75164 A2 | 10/2001 |
| WO | WO 2004/031347 A2 | 4/2004 |
| WO | WO 2005/032476 A2 | 4/2005 |
| WO | WO 2007/095113 | 8/2007 |

OTHER PUBLICATIONS

Golen et al. IGF-1 receptor activation and BCL-2 overexpression prevent early apoptotic events in human neuroblastoma, Cell death and Differentiation, 7, 654-665, 2000.*
Valverde et al. The brown adipose cell: a model for understanding the molecular mechanisms of insulin resistance. Acta Physiol. Scand. 183, 59-73, 2003.*
Qian et al. TNF alpha Induces and Insulin Inhibits Caspase 3-Dependent Adipocyte Apoptosis, Biochem. Biophys. Res. Commun. 284, 1176-1183, 2001.*
U.S. Appl. No. 11/708,402, filed Feb. 20, 2007, Nedivi and Fujino.
U.S. Appl. No. 60/772,450, filed Feb. 10, 2007, Nedivi.
Aebischer et al., "Long-Term Cross-Species Brain Transplantation of a Polymer-Encapsulated Dopamine-Secreting Cell Line," *Exp. Neurol.* 111:269-275, 1991.
Aberg et al., "Aspects of Growth Hormone and Insulin-Like Growth Factor-1 Related to Neuroprotection, Regeneration, and Functional Plasticity in the Adult Brain," *Sci. World J.* 6:53-80, 2006.
Baranes et al., "Reconstitution of the Hippocampal Mossy Fiber and Associational-Commissural Pathways in a Novel Dissociated Cell Culture System," *Proc. Natl. Acad. Sci. U.S.A.* 93:4706-4711, 1996.
Barbieri et al., "Insulin/IGF-1-Signaling Pathway: An Evolutionarily Conserved Mechanism of Longevity from Yeast to Humans," *Am. J. Physiol. Endocrinol. Metab.* 285:E1064-1071, 2003.
Barres et al., "Cell Death and Control of Cell Survival in the Oligodendrocyte Lineage," *Cell* 70:31-46, 1992.
Barres et al., "Multiple Extracellular Signals are Required for Long-Term Oligodendrocyte Survival," *Development* 118:283-295, 1993.
Brittberg et al., "Treatment of Deep Cartilage Defects in the Knee with Autologous Chondrocyte Transplantation," *N. Engl. J. Med.* 331:889-895, 1994.
Burgess et al., "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *J. Cell Biol.* 111:2129-2138, 1990.
Cantallops et al., "Postsynaptic CPG15 Promotes Synaptic Maturation and Presynaptic Axon Arbor Elaboration In Vivo," *Nature Neurosci.* 3:1004-1011, 2000.

(Continued)

*Primary Examiner*—Lorraine Spector
*Assistant Examiner*—Elly-Gerald Stoica
(74) *Attorney, Agent, or Firm*—Kristina Bieker-Brady; Clark & Elbing LLP

(57) ABSTRACT

Disclosed herein are CPG15 and CPG15-2 compounds and inhibitors that act as agonists and antagonists of the insulin receptor and insulin-like growth factor receptors, and the use of such compositions for the treatment of insulin and insulin-like growth factor-related diseases.

8 Claims, 7 Drawing Sheets

OTHER PUBLICATIONS

Charron et al., "The Morphogen Sonic Hedgehog Is an Axonal Chemoattractant that Collaborates with Netrin-1 in Midline Axon Guidance," *Cell* 113:11-23, 2003.

Cheng et al., "Complementary Gradients in Expression and Binding of ELF-1 and Mek4 in Development of the Topographic Retinotectal Projection Map," *Cell* 82:371-381, 1995.

Cline, "Dendritic Arbor Development and Synaptogenesis," *Curr. Opin. Neurobiol.* 11:118-126, 2001.

Corriveau et al., "Dynamic Regulation of cpg15 During Activity-Dependent Synaptic Development in the Mammalian Visual System," *J. Neurosci.* 19:7999-8008, 1999.

Davis, "Therapeutic Strategies to Retard Neuronal Cell Death in Neurodegenerative Diseases," *Curr. Opin. Investig. Drugs* 2:654-656, 2001.

Fujino et al., "Regulation of cpg15 by Signaling Pathways that Mediate Synaptic Plasticity," *Mol. Cell. Neurosci.* 24:538-554, 2003.

Gustafsson, "New Insights in Oestrogen Receptor (ER) Research—the Erbeta," *Eur. J. Cancer* 36 (Suppl. 4):S16, 2000.

Harwell et al., "Regulation of cpg15 Expression During Single Whisker Experience in the Barrel Cortex of Adult Mice," *J. Neurobiol.* 65:85-96, 2005.

Hevroni et al., "Hippocampal Plasticity Involves Extensive Gene Induction and Multiple Cellular Mechanisms," *J. Mol. Neurosci.* 10:75-98, 1998.

Hooper, "Determination of Glycosyl-Phosphatidylinositol Membrane Protein Anchorage," *Proteomics* 1:748-755, 2001.

Horellou et al., "In Vivo Release of DOPA and Dopamine from Genetically Engineered Cells Grafted to the Denervated Rat Striatum," *Neuron* 5:393-402, 1990.

Jellinger, "Cell Death Mechanisms in Neurodegeneration," *J. Cell. Mol. Med.* 5:1-17, 2001.

Johnson and Deckwerth, "Molecular Mechanisms of Developmental Neuronal Death," *Ann. Rev. Neurosci.* 16:31-46, 1993.

Kim et al., "SynGAP: A Synaptic RasGAP that Associates with the PSD-95/SAP90 Protein Family," *Neuron* 20:683-691, 1998.

Kirkwood et al., "The Dispersion of Neuronal Clones Across the Cerebral Cortex," *Science* 258:317-320, 1992.

Langer and Vacanti, "Tissue Engineering," *Science* 260:920-926, 1993.

Lee and Nedivi, "Extended Plasticity of Visual Cortex in Dark-Reared Animals May Result from Prolonged Expression of cpg15-Like Genes," *J. Neurosci.* 22:1807-1815, 2002.

Lois et al., "Germline Transmission and Tissue-Specific Expression of Transgenes Delivered by Lentiviral Vectors," *Science* 295:868-872, 2002.

Low, "Biochemistry of the Glycosyl-Phosphatidylinositol Membrane Protein Anchors," *Biochem J.* 244:1-13, 1987.

Marron et al., "Androgen-Induced Neurite Outgrowth is Mediated by Neuritin in Motor Neurones," *J. Neurochem.* 92:10-20, 2005.

Moen, "Directions in Gene Therapy," *Blood Cells* 17:407-416, 1991.

Mosmann, "Rapid Colorimetric Assay for Cellular Growth and Survival: Application to Proliferation and Cytotoxicity Assays," *J. Immunol. Methods* 65:55-63, 1983.

Naeve et al., "Neuritin: A Gene Induced by Neural Activity and Neurotrophins that Promotes Neuritogenesis," *Proc. Natl. Acad. Sci. U.S.A.* 94:2648-2653, 1997.

Nedivi et al., "Developmental Regulation of CPG15 Expression in *Xenopus*," *J. Comp. Neurol.* 435:464-473 (2001).

Nedivi et al., "Promotion of Dendritic Growth by CPG15, an Activity-Induced Signaling Molecule," *Science* 281:1863-1866, 1998.

Nedivi et al., "A Set of Genes Expressed in Response to Light in the Adult Cerebral Cortex and Regulated During Development," *Proc. Natl. Acad. Sci. U.S.A.* 93:2048-2053, 1996.

Offen et al., "Apoptosis as a General Cell Death Pathway in Neurodegenerative Diseases," *J. Neural Transm. Suppl.* 58:153-166, 2000.

Pawson and Nash, "Assembly of Cell Regulatory Systems Through Protein Interaction Domains," *Science* 300:445-452, 2003.

Placzek et al., "Mesodermal Control of Neural Cell Identity: Floor Plate Induction by the Notochord," *Science* 250:985-988, 1990.

Putz et al., "Soluble CPG15 Expressed During Early Development Rescues Cortical Progenitors from Apoptosis," *Nature Neurosci.* 8:322-331, 2005.

Rheinwald and Green, "Serial Cultivation of Strains of Human Epidermal Keratinocytes: The Formation of Keratinizing Colonies from Single Cells," *Cell* 6:331-337, 1975.

Ringstedt et al., "Slit Inhibition of Retinal Axon Growth and Its Role in Retinal Axon Pathfinding and Innervation Patterns in the Diencephalon," *J. Neurosci.* 20:4983-4991, 2000.

Rubin et al., "The Molecular Mechanisms of Neuronal Apoptosis," *Curr. Opin. Neurobiol.* 4:696-702, 1994.

Schubert et al., "Insulin Receptor Substrate-2 Deficiency Impairs Brain Growth and Promotes Tau Phosphorylation," *J. Neurosci.* 23:7084-7092, 2003.

Schwartz et al., "Do All Programmed Cell Deaths Occur Via Apoptosis?" *Proc. Natl. Acad. Sci. U.S.A.* 90:980-984, 1993.

Scott et al., "The Pendred Syndrome Gene Encodes a Chloride-Iodide Transport Protein," *Nature Genetics* 21:440-443, 1999.

Sobieszczuk and Wilkinson, "Masking of Eph Receptors and Ephrins," *Curr. Biol.* 9:R469-R470, 1999.

Tresco et al., "Polymer Encapsulated Neurotransmitter Secreting Cells. Potential Treatment for Parkinson's Disease," *ASAIO J.* 38:17-23, 1992.

Udin, "CPG15 and the Dynamics of Retinotectal Synapses," *Nature Neurosci.* 3:971-972, 2000.

Vermes et al., "A Novel Assay for Apoptosis. Flow Cytometric Detection of Phosphatidylserine Expression on Early Apoptotic Cells Using Fluorescein Labelled Annexin V," *J. Immunol. Methods* 184:39-51, 1995.

Walsh and Cepko, "Widespread Dispersion of Neuronal Clones Across Functional Regions of the Cerebral Cortex," *Science* 255:434-440, 1992.

Walton et al., "Annexin V Labels Apoptotic Neurons Following Hypoxia-Ischemia," *NeuroReport* 8:3871-3875, 1997.

Wang and Tessier-Lavigne, "*En Passant* Neurotrophic Action of an Intermediate Axonal Target in the Developing Mammalian CNS," *Nature* 401:765-769, 1999.

Winn et al., "Behavioral Recovery Following Intrastriatal Implantation of Microencapsulated PC12 Cells," *Exp. Neurol.* 113:322-329, 1991.

Zhou and Tang, "Huperzine A Attenuates Apoptosis and Mitochondria-Dependent Caspase-3 in Rat Cortical Neurons," *FEBS Lett.* 526:21-25, 2002.

Zhou et al., "Isolation and Cloning of a Novel Human cDNA Encoding Rat Neuritin Homolog," NCBI Accession No. AAF62371, 2000.

Blast two sequences results, Zhou et al. NCBI Accession No. AAF62371 vs. SEQ ID No. 1 of U.S. Appl. No. 10/670,991, 2006.

International Search Report for PCT/US03/30152 dated Dec. 9, 2004.

International Search Report for PCT/US07/03561 completed Jun. 30, 2008.

International Preliminary Report on Patentability for PCT/US07/03561 issued Nov. 4, 2008.

Written Opinion of the International Searching Authority for PCT/US07/03561 completed Jun. 30, 2008.

International Preliminary Examination Report from PCT/US2003/30152, completed Sep. 10, 2007.

International Search Report from PCT/US2004/32179, completed Nov. 5, 2007.

International Preliminary Report on Patentability from PCT/US2004/32179, issued Dec. 6, 2007.

Written Opinion of the International Searching Authority from PCT/US2004/32179, completed Nov. 5, 2007.

Sequence ID No. 2975 from WO 01/53312, published Jul. 26, 2001.

\* cited by examiner

Figure 1
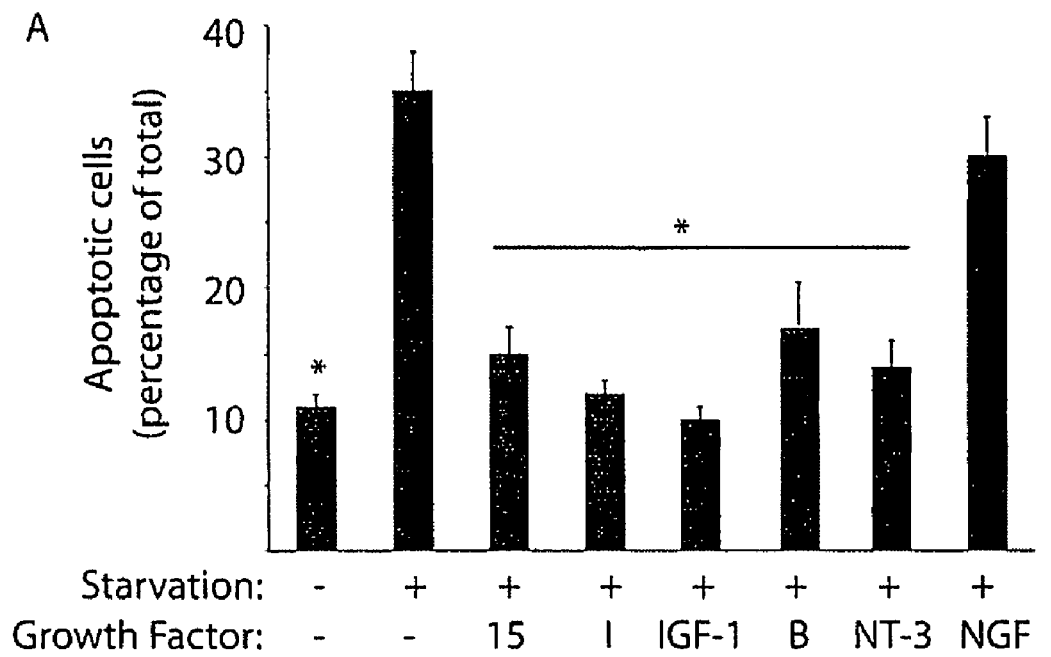
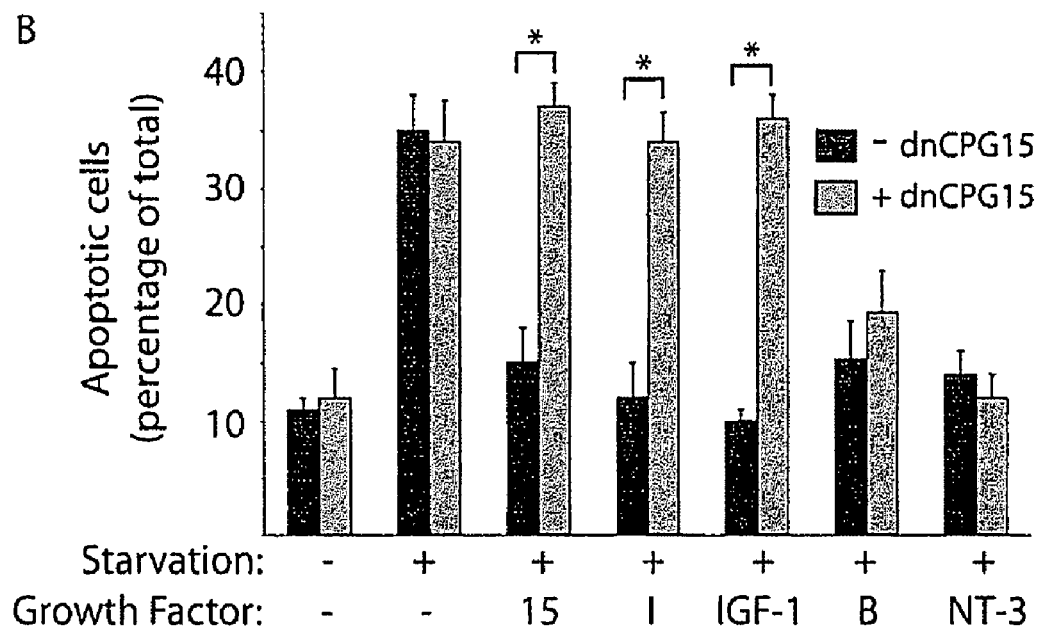

Figure 3
A
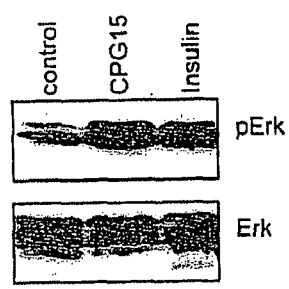
B
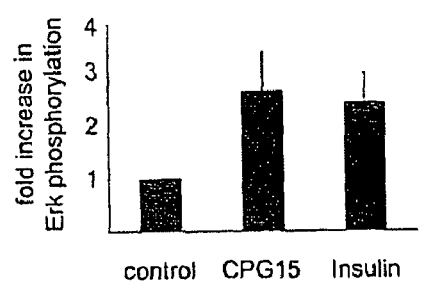
C
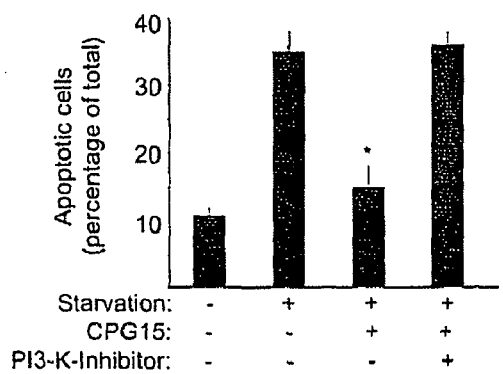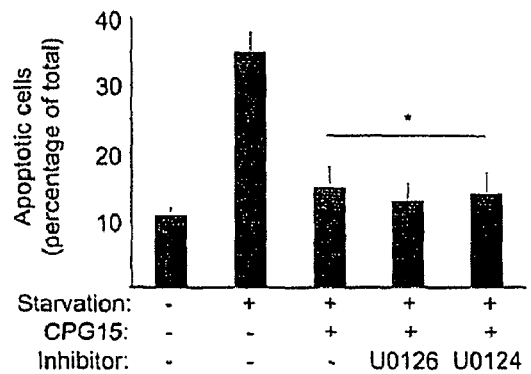

Figure 4A

Human CPG15 (SEQ ID NO: 4)

MGLKLNGRYISLILAVQIAYLVQAVRAAGKCDAVFKGFSDCLLKLGDSM
ANYPQGLDDKTNIKTVCTYWEDFHSCTVTALTDCQEGAKDMWDKLRKE
SKNLNIQGSLFELCGSGNGAAGSLLPAFPVLLVSLSAALATWLSF

Figure 4B

Dominant Negative CPG15 (SEQ ID NO: 5)

AGGTDYKDDDDKCDAVFKGFSDCLLKLGDSMANYPQGLDDKTNIKTVC
TYWEDFHSCTVTALTDCQEGAKDMWDKLRKESKNLNIQGSLFELCGSGN

Figure 5A human cpg15-2 (NM_198443)

```
  1  accccccagctcccatccaatcaccgtccccctccggggctggggacgggctgcac      60

61  tccaagcagctagctccctgcactagctctcagccaggatgatgcgctgcgccgc     120
                                       M  M  R  C  R  R 121  cgctgctgctgcgcaacctgccctgaggccgttgctgcccctgtc             180
     R  C  C  R  Q  P  P  H  A  L  R  P  L  L  L  P  L  V 181  cttttacccccctggcagcagctgcagcgggcccaaaacgatgtgacaccatataccag    240
     L  L  P  P  L  A  A  A  A  G  P  N  R  C  D  T  I  Y  Q 241  ggcttcgccgagtgtcttcatccgctgggggacagcagcatgggccggaggcgagctgag    300
     G  F  A  E  C  L  I  R  L  G  D  S  M  G  R  G  G  E  L  E 301  accatctgcagtcttgaatgacttccatgcctgtgcctcttcaggtcctcaggtcctgt    360
     T  I  C  R  S  W  N  D  F  H  A  C  A  S  Q  V  L  S  G  C 361  ccggagaggcagtcagttgtgggaatcactacagcaagaagctcgccaggccccgt      420
     P  E  E  A  A  A  V  W  E  S  L  Q  Q  E  A  R  Q  A  P  R 421  ccgaataacttgcacactcgtgcgtgccctgccatgtgcgccacaggc           480
     P  N  N  L  H  T  L  C  G  A  P  V  H  V  R  E  R  G  T  G 481  tccgaaaccaaccaggagacgctgcggctacagcgcctgcactcccatggcccctgcg    540
     S  E  T  N  Q  E  T  L  R  A  T  A  P  A  L  P  M  A  P  A 541  ccccactgctgcgcggctgctctcggctctgaccctcctgaggccctggcctagctc    600
     P  P  L  L  A  A  A  L  A  L  A  Y  L  L  R  P  L  A  *

601  gttgggttgggtagcagcgcccgtacctccagcctcctctggcggtggtgtcaggct     660

661  ctgcagagagcgcagcaggggctcttccattaaaggtattatatttgt              705
```

Figure 5B mouse cpg15-2 (AK090312)

```
  1  gacagccagggatgatgtgcaactgctgctgccactgccactggccgccgcgcgctgtcagcggc      60
        M  M  C  N  C  H  C  H  W  R  R  C  Q  R  L 61  tacccTgtgcccTgacgctgtgctgctactaccactcgctactggccctctgagggcccaa       120
        P  C  A  L  T  L  L  L  L  P  L  A  V  A  S  E  G  P  N 121  accgctgtgataccatataccaaggcttTgctgaatgtctcatccgctggggggatggca      180
        R  C  D  T  I  Y  Q  G  F  A  E  C  L  I  R  L  G  D  G  M 181  tgggTcgaggaggcgagcTacagacTgtcTcagatccTggaaTgacttccacgcctgtg      240
        G  R  G  G  E  L  Q  T  V  C  R  S  W  N  D  F  H  A  C 241  ccTctcTgggtcctgtcaggctgccgcccagaggaggcggctgcagTgTggaagtcactgcagc      300
        S  R  V  L  S  G  C  P  E  E  A  A  A  V  W  E  S  L  Q  Q 301  aagaagctcgcgcgcccacaccccagtaatTtgcacaTccTctgTggcgctccTga      360
        E  A  R  R  A  P  H  P  D  N  L  H  I  L  C  G  A  P  V  S 361  gTgTTcgggagcggatTgcTgcccagaccaaccaggagaccacTacggccacactggccacagcTc      420
        V  R  E  R  I  A  G  P  E  T  N  Q  E  T  L  R  A  T  A  P 421  cTgcacTggcTccagTccagcccctgTTgTgccgccgcTTcTagcgcTTgccTgcc     480
        A  L  A  P  A  P  A  P  V  L  L  A  A  A  L  A  L  A  C  L 481  TccTgggcTccTgggccTaaacagTgTccTggTTggccagcccTTgccTgccTcccaT      540
        L  G  P  L  A  *

541  cacTgcaTgcagTggcTgccaTgTgagTcTgcagTaTgcacacTTTcaTTaaaggTaT      600

601  TTaTaTTc  608
```

Figure 6

Mouse CPG15 (NP_705757)

```
1   MGLKLNGRYI SLILAVQIAY LVQAVRAAGK CDAVFKGFSD
41  CLLKLGDSMA NYPQGLDDKT NIKTVCTYWE DFHSCTVTAL
81  TDCQEGAKDM WDKLRKESKN LNIQGSLFEL CGSSNGAAGS
121 LLPALSVLLV SLSAALATWF SF
```

US 7,884,078 B2

CPG15 COMPOUNDS AS INSULIN RECEPTOR AND INSULIN-LIKE GROWTH FACTOR RECEPTOR AGONISTS

CROSS REFERENCE TO RELATED APPLICATIONS

This application claims the benefit of the filing date of U.S. Provisional Application No. 60/772,450, Feb. 10, 2006, herein incorporated by reference.

STATEMENT AS TO FEDERALLY SPONSORED RESEARCH

This invention was made in part with support from the Government through NIH Grant No. R01-EY011894. The Government has certain rights in the invention.

BACKGROUND OF THE INVENTION

Insulin is a potent metabolic and growth promoting hormone that acts on cells to stimulate glucose, protein, and lipid metabolism, as well as RNA and DNA synthesis. A well-known effect of insulin is the regulation of glucose levels in the body, which occurs predominantly in liver, fat, and muscle tissue. In the liver, insulin stimulates glucose metabolism into glycogen and inhibits the production of glucose. In muscle and fat tissue, insulin stimulates glucose uptake, storage, and metabolism. Defects in insulin-mediated regulation of blood glucose levels are very common and give rise to disorders such as diabetes and obesity.

Insulin initiates signal transduction in target cells by binding to a specific cell-surface receptor, the insulin receptor (IR). Insulin binding leads to conformational changes in the extracellular domain of the IR, which result in activation of the receptor's tyrosine kinase activity. This, in turn, leads to tyrosine kinase autophosphorylation of the IR, and the recruitment and binding of effector molecules that contain SH2 domains such as phophoinositol-3-kinase (PI3K), Ras GTPase-activating protein, and phospholipase C to the IR. The subsequent phosphorylation and activation of effector molecules (e.g., Ras), leads to phosphorylation of downstream signaling molecules (e.g., ERK, Raf1, MEK, and Akt), and activates immediate/early gene transcription (e.g., c-fos, pip92, egr-1, c-myc, c-jun, jun-B, and fra-1).

Insulin-like growth factor 1 (IGF-1) is a small, single-chain protein that is involved in the regulation of many aspects of tissue growth and repair. Similar to insulin, IGF-1 is thought to have a role in metabolic pathways. IGF-1 also stimulates cell differentiation and cell proliferation and is required by most mammalian cell types for sustained proliferation. IGF-1 has been implicated in various forms of cancer including prostate, breast, colon, ovarian and lung cancers. IGF-1 is similar in size, sequence, and structure to insulin, but has a much lower affinity for the IR. Instead, IGF-1 generally binds to the IGF-1 receptor (IGF-1R).

The insulin/IGF-1 family of receptors consists of three separate receptors that can bind insulin and IGF-1 with varying affinity: insulin receptor (IR), IGF-1 receptor (IGF-1R), and IGF-2 receptor (IGF-2R). A fourth, orphan member of the family is insulin receptor-related receptor (IRR), for which the endogenous ligand is unknown. Three of the four receptors (IR, IGF-1R, and IRR) belong to the family of ligand-activated receptor tyrosine kinases. In contrast, the IGF-2 receptor is a monomeric receptor with a large extracellular domain and no intrinsic signaling capabilities; it serves mainly as a ligand-clearing receptor. The IR and the IGF-1R are expressed at the cell surface as homodimers composed of two identical monomers, or as heterodimers composed of two different receptor monomers (e.g., IGF-1R/IR). These latter receptors are called hybrid receptors and are widely distributed in mammalian tissue and behave in a manner similar to IGF-1R, with respect to ligand-induced autophosphorylation.

Both IGF-1R and IR receptors are composed of two α and two β subunits which form a disulfide-linked heterotetramer (β-α-α-β). These receptors have an extracellular ligand binding domain, a single transmembrane domain, and a cytoplasmic domain displaying the tyrosine kinase activity. The extracellular domain is composed of the entire α subunits and a portion of the N-terminus of the β subunits, while the intracellular portion of the β subunits contains the tyrosine kinase domain.

While similar in structure, IGF-1R and IR serve different physiological functions. IR is primarily involved in metabolic functions whereas IGF-1R mediates growth and differentiation. However, both insulin and IGF-1 can induce mitogenic and metabolic effects via the receptors.

In view of the importance of the signaling pathways mediated by IR and IGF-1R and the role for these receptor proteins in such disorders as diabetes, obesity, neurological conditions, cancer and other cellular proliferative diseases, agonists and antagonists that modulate the signaling activity of each receptor are needed.

SUMMARY OF THE INVENTION

Insulin and IGF-1 work through their cognate receptors, IR and IGF-1R, respectively, to regulate a variety of metabolic and proliferative signaling pathways. These pathways are involved in the regulation of a variety of cellular processes including the regulation of glucose levels, lipid metabolism, DNA and RNA synthesis, and cellular proliferation. We have discovered that insulin binding receptor activators (IBRA), such as soluble-CPG15 (s-CPG15), CPG15-2, or soluble-CPG15-2 can bind (directly or indirectly) to insulin-binding receptors, such as IR and IGF-1R, either separately or together, to regulate these signaling pathways. s-CPG15 and s-CPG15-2 share substantial sequence identity and both function as survival factors that can rescue cells from cell death and promote cell survival and differentiation. We have discovered that s-CPG15, CPG15-2, and s-CPG15-2 can act as agonists (either directly or indirectly) to the insulin-binding receptors, such as IR or IGF-1R, or both, and can promote the activation of these receptors. This agonistic activity can result in the recruitment of downstream signaling proteins and the activation of signaling pathways associated with the proteins. In addition, we have discovered that inhibitors of s-CPG15 or CPG15-2 (including inhibitors of s-CPG15-2), such as dominant negative forms of CPG15 or CPG15-2, can block the function of insulin and IGF-1 but not that of other growth factors, such as BDNF and NT-3, in a cell survival assay. Therefore, s-CPG15 or s-CPG15-2 compounds and inhibitors of s-CPG15 or CPG15-2 (including inhibitors of s-CPG15-2) are useful as specific agonists or antagonists, respectively, of the insulin-binding receptors and can be used to treat or prevent disorders that result from aberrant signaling from any member of this family of receptors.

Accordingly, in a first aspect, the invention features a method of increasing (e.g., by at least 20%, 30%, 40%, 50%, 60%, 70%, 80%, 90% or more) the biological activity of an insulin-binding receptor in a mammalian cell (e.g., insulin receptor, IGF-1R, or IGF-2R). The method includes contacting the cell with a purified insulin-binding receptor activator (IBRA) having 1) at least one of the following activities: the ability to promote cell survival; the ability to promote neurite outgrowth; or the ability to promote reduction of cell death; and 2) the ability to bind to or activate an insulin-binding receptor. The IBRA of any of the above aspects of the present invention can be an s-CPG15 compound, an s-CPG15-2 compound, a CPG15-2 compound, or a cpg15 nucleic acid molecule which encodes a CPG15 polypeptide or a cpg15-2 nucleic acid molecule which encodes CPG15-2 protein, wherein the IBRA can bind to or activate an insulin-binding receptor (e.g., insulin receptor, IGF-1R, and IGF-2R). In desired embodiments, the IBRA binds to or activates the insulin receptor or IGF-1 receptor. Desirably, the IBRA of the present invention is an s-CPG-15 or s-CPG15-2 compound; more desirably, the IBRA is an s-CPG15 or s-CPG15-2 polypeptide. In one example, the s-CPG15 polypeptide comprises the sequence of SEQ ID NO: 1. In another example, the s-CPG15-2 polypeptide comprises the sequence of SEQ ID NO: 9.

In other embodiments of the invention, the IBRA is an s-CPG15 or an s-CPG15-2 polypeptide that lacks a signal sequence, and more desirably, the s-CPG15 or s-CPG15-2 polypeptide lacks a signal sequence and a GPI linkage sequence. In related embodiments, the IBRA is an s-CPG15 or an s-CPG15-2 polypeptide that has a post-translational modification; more desirably, the s-CPG15 or s-CPG15 polypeptide post-translation modification is the attachment of a membrane component (e.g., lipid, cholesterol, glycolipid, phospholipid, lipoprotein, and liposaccharide).

The biological activity of the IBRA can also include any one or more of the following: binding of receptor substrate molecules (e.g., IRS1, IRS2, IRS3, IRS4, PI3K, Shc, and Grb2); phosphorylation of receptor substrate molecules or downstream molecules (e.g., Raf1, MEK, ERK, and Akt); glucose uptake; insulin-induced immediate/early gene expression; or ligand internalization. The cell used in the above aspect of the invention can be any cell (e.g., fibroblast, epithelial cell, endothelial cell, hepatocyte, muscle cell, neuronal cell, adipocyte, and a hematopoietic cell); more desirably, the cell is a neuron or an adipocyte.

In another aspect, the invention features a method of decreasing (e.g., by at least 10%, 20%, 30%, 40%, 50%, 60%, 70%, 80%, or 90% or more) the biological activity of an insulin-binding receptor (e.g., IR, IGF-1R, or IGF-2R) in a mammalian cell by contacting the cell with an insulin-binding receptor inhibitor (IBRI) which has the ability to inhibit insulin-binding receptor biological activity. In desired embodiments, the IBRI inhibits the insulin receptor or the IGF-1 receptor. The IBRI can be an inhibitor of s-CPG15 or an inhibitor of CPG15-2 (e.g., an inhibitor of s-CPG15-2 or CPG15-2 expression levels or biological activity). In desired embodiments, the IBRI is a dominant negative form of CPG15 or a dominant negative form of CPG15-2. In one desired embodiment, the IBRI is a dominant negative form of CPG15 comprising the sequence of SEQ ID NO: 5. In another embodiment, the IBRI binds to, but does not activate, the insulin receptor or the IGF-1 receptor.

In another aspect, the invention features a method of increasing the insulin or IGF-1 sensitivity in a cell by contacting the cell with an IBRI, which binds the IGF-2 receptor on the cell and decreases the insulin or IGF-1 uptake by the cell. In another aspect, the IBRI is a dominant negative form of CPG15 (e.g., a truncated form of CPG15 comprising the sequence of SEQ ID NO: 5). In desired embodiments, insulin or IGF-1 uptake is reduced (e.g., by at least 10%, 20%, 30%, 40%, 50%, 60%, 70%, or 80%) in a cell. The cell used in the above aspect of the invention can be any cell (e.g., fibroblast, epithelial cell, endothelial cell, hepatocyte, muscle cell, neuronal cell, adipocyte, and a hematopoietic cell); more desirably, the cell is a neuron or an adipocyte.

In another aspect, the invention features a method of treating or preventing insulin deficiency or insulin resistance disorder in subject, by administering to a subject an IBRA having 1) at least one of the following: the ability to promote cell survival; the ability to promote neurite outgrowth; or the ability to promote reduction of cell death; and 2) the ability to bind to or activate an insulin-binding receptor, wherein the IBRA is delivered in an amount and for time sufficient to treat or prevent insulin deficiency or insulin resistance in a subject. In desired embodiments, the insulin deficiency or insulin resistance in a subject is reduced by at least 10%, 20%, 30%, 40%, 50%, 60%, 70%, 80%, or even 90% or more. This method can be used to treat or prevent, for example, Type 1 or Type 2 diabetes, hyperglycemia, hyperinsulinemia, dyslipidemia, obesity, polycystic ovarian disease, hypertension, cardiovascular disease, and syndrome X. This method can also be used to treat or prevent Alzheimer's disease, diabetic neuropathy, appetite control, neurodegeneration, and learning and memory impairment.

In another aspect, the invention provides a method of treating or preventing an IGF-1 deficiency or IGF-1 resistance disorder in a subject by administering to the subject an IBRA having 1) at least one of the following: the ability to promote cell survival; the ability to promote neurite outgrowth; or the ability to promote reduction of cell death; and 2) the ability to bind to or activate an insulin-binding receptor, when the IBRA is delivered in an amount and for time sufficient to treat or prevent IGF-1 deficiency or IGF-1 resistance in a subject. In desired embodiments, the IGF-1 deficiency or IGF-1 resistance in a subject is reduced by at least 10%, 20%, 30%, 40%, 50%, 60%, 70%, 80%, or even 90% or more. This method can be used to treat or prevent, for example, amyotrophic lateral sclerosis, diabetic motor neuropathy, osteoporosis, immune modulation disorders, nephrotic syndrome, small stature, and decreased muscle mass.

In another aspect, the present invention provides a method of maintaining glucose levels within a normal range in a subject having elevated blood levels by administering to the subject an IBRA having 1) at least one of the following: the ability to promote cell survival; the ability to promote neurite outgrowth; or the ability to promote reduction of cell death; and 2) the ability to bind to or activate an insulin-binding receptor, when the IBRA is delivered in an amount and for time sufficient to maintain blood glucose levels within a normal range in a subject. In desired embodiments, the maintenance of blood glucose levels within a normal range in a subject is improved by at least 10%, 20%, 30%, 40%, 50%, 60%, 70%, 80%, or even 90% or more.

In another aspect, the invention features a method of achieving weight loss or appetite suppression in a subject, by administering to a subject an IBRA having 1) at least one of the following: the ability to promote cell survival; the ability to promote neurite outgrowth; or the ability to promote reduction of cell death; and 2) the ability to bind to or activate an insulin-binding receptor, when the IBRA is delivered in an amount and for time sufficient to achieve weight loss or appetite suppression in a subject. In desired embodiments, the weight loss or appetite suppression is increased by at least 10%, 20%, 30%, 40%, or even 50% or more.

In desired embodiments any of the above methods, the IBRA binds to or activates the insulin receptor or the IGF-1 receptor. The IBRA of any of the above aspects of the present invention can be an s-CPG15 compound, an s-CPG15-2 compound, a CPG15-2 compound, or a cpg15 nucleic acid molecule which encodes a CPG15 polypeptide or a cpg15-2 nucleic acid molecule which encodes CPG15-2 protein, wherein the IBRA can bind to or activate an insulin-binding receptor (e.g., insulin receptor, IGF-1R, and IGF-2R). Desirably, the IBRA of the present invention is an s-CPG-15 or s-CPG15-2 compound; more desirably, the IBRA is an s-CPG15 or s-CPG15-2 polypeptide. In one example, the s-CPG15 polypeptide comprises the sequence of SEQ ID NO: 1. In another example, the s-CPG15-2 polypeptide comprises the sequence of SEQ ID NO: 9.

In other embodiments of the invention, the IBRA is an s-CPG15 or an s-CPG15-2 polypeptide that lacks a signal sequence, and more desirably, the s-CPG15 or s-CPG15-2 polypeptide lacks a signal sequence and a GPI linkage sequence. In related embodiments, the IBRA is an s-CPG15 or an s-CPG15-2 polypeptide that has a post-translational modification; more desirably, the s-CPG15 or s-CPG15 polypeptide post-translation modification is the attachment of a membrane component (e.g., lipid, cholesterol, glycolipid, phospholipid, lipoprotein, and liposaccharide).

The present invention also provides a method for maintaining blood glucose levels within a normal range in a subject having reduced blood glucose levels by administering to the subject an IBRI which has the ability to inhibit insulin-binding receptor biological activity, when administered in an amount and for a time sufficient to maintain blood glucose levels within a normal range in the subject. In desired embodiments, the maintenance of blood glucose levels in a normal range in a subject is improved by at least 10%, 20%, 30%, 40%, 50%, 60%, 70%, 80%, or 90% or more.

The invention further provides a method of treating or preventing insulin excess disorder in a subject by administering to the subject an IBRI which has the ability to inhibit insulin-binding receptor biological activity, when administered in an amount and for time sufficient to treat or prevent insulin excess disorder in the subject. In desired embodiments, the insulin excess disorder in a subject is improved by at least 10%, 20%, 30%, 40%, 50%, 60%, 70%, 80%, or 90%. This method can be used to treat or prevent, for example, hypoglycemia, insulinomas, insulin and hypoglycemia drug overdose, gastic dumping syndrome, and congenital hyperinsulism.

The invention further provides a method of treating or preventing IGF-1 excess disorder in a subject by administering to the subject an IBRI which has the ability to inhibit insulin-binding receptor biological activity, when administered in an amount and for time sufficient to treat or prevent IGF-1 excess disorder in the subject. In desired embodiments, the insulin excess disorder in a subject is improved by at least 10%, 20%, 30%, 40%, 50%, 60%, 70%, 80%, or 90% or more. This method of the present invention can be used to prevent or treat a proliferative disorder (e.g., cancer). In desired embodiments, the method of the invention is used to treat or prevent prostate, breast, colon, ovarian, and lung cancer. This method can also be used to treat or prevent acromegaly, gigantism, psoriasis, atherosclerosis, smooth muscle restenosis, and diabetes.

In desired embodiments on the above methods, the IBRI inhibits the insulin receptor or the IGF-1 receptor. The IBRI can be an inhibitor of s-CPG15 or an inhibitor of CPG15-2 (e.g., an inhibitor of s-CPG15-2 or CPG15-2 expression levels or biological activity). In desired embodiments, the IBRI is a dominant negative form of CPG15 or a dominant negative form of CPG15-2. In one desired embodiment, the IBRI is a dominant negative form of CPG15 comprising the sequence of SEQ ID NO: 5. In another embodiment, the IBRI binds to, but does not activate, the insulin receptor or the IGF-1 receptor.

For any of the above aspects, the insulin-binding receptor can be any mammalian receptor that binds to insulin, such as, IR, IGF-1R, or IGF-2R.

The invention also provides a kit for the treatment or prevention of an insulin deficiency or insulin resistance disorder, which contains an IBRA and instructions for the use of the IBRA in the treatment or prevention of the insulin deficiency or insulin resistance disorder.

The invention also provides a kit for the treatment or prevention of an IGF-1 deficiency or IGF-1 resistance disorder, which contains an IBRA and instructions for the use of the IBRA in the treatment or prevention of IGF-1 deficiency or IGF-1 resistance disorder.

In preferred embodiments of any of the above kits, the IBRA can be an s-CPG15 compound, an s-CPG15-2 compound, a CPG15-2 compound, or a cpg15 nucleic acid molecule which encodes a CPG15 polypeptide or a cpg15-2 nucleic acid molecule which encodes CPG15-2 protein, wherein the IBRA can bind to or activate an insulin-binding receptor (e.g., insulin receptor, IGF-1R, and IGF-2R). In desired embodiments, the IBRA binds to or activates the insulin receptor or IGF-1 receptor. Desirably, the IBRA of the present invention is an s-CPG-15 or s-CPG15-2 compound; more desirably, the IBRA is an s-CPG15 or s-CPG15-2 polypeptide. In one example, the s-CPG15 polypeptide comprises the sequence of SEQ ID NO: 1. In another example, the s-CPG15-2 polypeptide comprises the sequence of SEQ ID NO: 9.

In other embodiments of the invention, the IBRA is an s-CPG15 or an s-CPG15-2 polypeptide that lacks a signal sequence, and more desirably, the s-CPG15 or s-CPG15-2 polypeptide lacks a signal sequence and a GPI linkage sequence. In related embodiments, the IBRA is an s-CPG15 or an s-CPG15-2 polypeptide that has a post-translational modification; more desirably, the s-CPG15 or s-CPG15 polypeptide post-translation modification is the attachment of a membrane component (e.g., lipid, cholesterol, glycolipid, phospholipid, lipoprotein, and liposaccharide).

In addition, the invention provides a kit for the treatment or prevention of an insulin excess disorder, which contains an IBRI and instructions for the use of the IBRI in the treatment or prevention of insulin excess disorder.

The invention also provides a kit for the treatment or prevention of an IGF-1 excess disorder, which contains an IBRI and instructions for the use of the IBRI in the treatment or prevention of IGF-1 excess disorder.

In desirable embodiments of any of the above kits, the IBRI can be an inhibitor of s-CPG15 or an inhibitor of CPG15-2 (e.g., an inhibitor of s-CPG15-2 or CPG15-2 expression levels or biological activity). In desired embodiments, the IBRI is a dominant negative form of CPG15 or a dominant negative form of CPG15-2. In one desired embodiment, the IBRI is a dominant negative form of CPG15 comprising the sequence of SEQ ID NO: 5. In another embodiment, the IBRI binds to, but does not activate, the insulin receptor or the IGF-1 receptor.

The invention also provides a method for increasing the biological activity of an insulin-binding receptor in a cell by administering to the cell a nucleic acid molecule comprising a nucleic acid sequence which encodes a polypeptide comprising an amino acid sequence having at least 85%, 95%, 96%, 97%, 98%, 99% or 100% identity to the sequence of SEQ ID NO: 2, 3, 4, or 10.

The invention further provides a method for treating or preventing an insulin deficiency or insulin resistance disorder in a subject by administering to the subject a nucleic acid molecule comprising a nucleic acid sequence which encodes a polypeptide comprising an amino acid sequence having at least 85%, 95%, 96%, 97%, 98%, 99% or 100% identity to the sequence of SEQ ID NO: 2, 3, 4, or 10. The method can be used to treat or prevent, for example, Type I or Type II diabetes, hyperglycemia, hyperinsulinemia, dyslipidemia, obesity, polycystic ovarian disease, hypertension, cardiovascular disease, and syndrome X. The method can also be used to treat or prevent Alzheimer's disease, diabetic neuropathy, appetite control, neurodegeneration, and learning and memory impairment.

The invention further provides a method for treating or preventing an IGF-1 deficiency or IGF-1 resistance disorder in a subject by administering to the subject a nucleic acid molecule comprising a nucleic acid sequence which encodes a polypeptide comprising an amino acid sequence having at least 85%, 95%, 96%, 97%, 98%, 99% or 100% identity to the sequence of SEQ ID NO: 2, 3, 4, or 10. The method can be used to treat or prevent, for example, amyotrophic lateral sclerosis, diabetic motor neuropathy, osteoporosis, immune modulation disorders, nephrotic syndrome, small stature, and decreased muscle mass.

The invention further provides a method for maintaining blood glucose levels within a normal range in a subject by administering to the subject a nucleic acid molecule comprising a nucleic acid sequence which encodes a polypeptide comprising an amino acid sequence having at least 85%, 95%, 96%, 97%, 98%, 99% or 100% identity to the sequence of SEQ ID NO: 2, 3, 4, or 10.

Our discovery of the ability of s-CPG15 and s-CPG15-2 to bind to or activate members of the insulin-binding receptor family, such as IR or IGF-1R, provides a novel surprising mechanism for regulation of the insulin-binding receptor family.

Unless defined otherwise, all technical and scientific terms used herein have the same meaning as commonly understood to one of ordinary skill in the art. Unless otherwise indicated, such as through context, as used herein, the following terms are intended to have the following meanings in interpreting the present invention.

By "antisense nucleobase oligomer" is meant a nucleobase oligomer, regardless of length, that is complementary to the coding strand or mRNA of a gene that encodes a protein having s-CPG15 or CPG15-2 biological activity. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified (e.g., phosphorothiates, phosphorodithiates, and phosphotriesters) and unmodified, oligonucleotides with modified (e.g., morpholino linkages and heteroatom backbones) or unmodified backbones, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. Patent Application Publication Nos. 20030114412 and 20030114407, incorporated herein by reference. The nucleobase oligomer can also be targeted to the translational start and stop sites. Preferably the antisense nucleobase oligomer comprises from about 8 to 30 nucleotides. The antisense nucleobase oligomers can also contain at least 40, 60, 85, 120, or more consecutive nucleotides that are complementary to the mRNA or DNA that encodes a protein having s-CPG15 or CPG15-2 biological activity, and may be as long as the full-length mRNA or gene).

By "apoptosis" or "apoptotic cell death" is meant the process of cell death wherein a dying cell displays a set of well-characterized biochemical hallmarks that include cell membrane blebbing, cell soma shrinkage, chromatin condensation, and DNA laddering. Cells that die by apoptosis include neurons (e.g., during the course of neurodegenerative diseases or neurogenesis), cardiomyocytes (e.g., after myocardial infarction or over the course of congestive heart failure), immune cells (e.g., after HIV infection), and cancer cells (e.g., after exposure to radiation or chemotherapeutic agents).

By "candidate plasticity gene 15" or "cpg15" is meant any nucleic acid sequence that encodes a protein that is substantially identical to any of the following: rat CPG15/neuritin (Nedivi et al., Proc. Natl. Acad. Sci. USA. 93:2048-2053, 1996; Hevroni et al., J. Mol. Neurosci. 10:75-98, 1998; GenBank accession number U88958), mouse CPG15 (GenBank accession number BC035531); human CPG15/neuritin (Naeve et al., Proc. Natl. Acad. Sci. U.S.A. 94:2648-2653, 1997; SEQ ID NO: 4; GenBank accession number NM016588 and AF136631), Xenopus CPG15 (Nedivi et al., J. Comp. Neurol. 435:464-473, 2001; GenBank accession number AF378092), and cat CPG15 (Corriveau et al., J. Neurosci. 19:7999-8008, 1999). The term "cpg15" includes nucleic acid sequence encoding any form of the above proteins, including the membrane bound and soluble forms and any modifications or conservative substitutions to the proteins.

By "CPG15" is meant a protein that is substantially identical to any of the following: rat CPG15/neuritin (Nedivi et al., Proc. Natl. Acad. Sci. U.S.A., 93:2048-2053, 1996; Hevroni et al., J. Mol. Neurosci. 10:75-98, 1998; GenBank accession number U88958), mouse CPG15 (GenBank accession number NP_705757; SEQ ID NO: 10); human CPG15/neuritin (Naeve et al., Proc. Natl. Acad. Sci. U.S.A. 94:2648-2653, 1997; SEQ ID NO: 4; GenBank accession number NM016588 and AF136631), Xenopus CPG15 (Nedivi et al., J. Comp. Neurol., 435:464-473, 2001; GenBank accession number AF378092), and cat CPG15 (Corriveau et al., J. Neurosci. 19:7999-8008, 1999), and includes a GPI consensus sequence and a secretion signal sequence. The term CPG15 includes naturally occurring forms of the protein, non-natural or synthetic forms of the protein, analogs and homologs of CPG15, and any conservative substitutions or modifications as known in the art and described herein. CPG15 is also sometimes referred to as neuritin. As used herein, CPG15 refers to the complete, unprocessed form of the protein including the GPI consensus sequence and the secretion signal sequence, or the membrane bound form of the protein.

By "soluble cpg15 (s-CPG15)" is meant any soluble form of a CPG15 protein described above that lacks the secretion signal sequence, or lacks both the secretion signal sequence and the GPI linkage sequence, and includes an amino acid sequence that is substantially identical to the following core domain: AGKCDAVFKGFSDCLLKLGDS-MANYPQGLDDKTNIKTVCTYWEDFH-SCTVTALTDCQEGAKDMWDKLRKESKNL-NIQGSLFELCGSG (SEQ ID NO: 1) (human) or the equivalent core domain for any of the CPG15 proteins described above. An asparagine residue (N) can also be present at the carboxy terminus of the protein. A methionine residue (M) can be inserted at the amino terminus of the core domain sequence. s-CPG15 can refer to the naturally occurring forms of the protein or to any non-natural or synthetic form of the protein and any conservative substitutions or modifications as known in the art and described herein.

Additional details regarding CPG15 and s-CPG15 proteins can be found in U.S. Patent Application Publication No. 20040176291 and PCT Publication No. WO 2004/031347.

By "s-CPG15 compound" is meant any small molecule chemical compound, antibody, nucleic acid molecule, or polypeptide, or fragment thereof that is substantially identical to an s-CPG-15 amino acid or nucleic acid sequence or that has substantial identity to the secondary or tertiary structure of an s-CPG15 protein, or fragments or derivatives thereof; and that has at least one s-CPG15 biological activity, as described below. For example, an s-CPG15 compound may not have extensive primary sequence identity to s-CPG15 but its secondary structure may closely resemble the secondary structure of s-CPG15. Examples of s-CPG15 compounds include s-CPG15 polypeptides, fragments or derivatives thereof. A preferred s-CPG15 compound is a soluble CPG15 polypeptide. An s-CPG15 compound may also have the ability to competitively inhibit the biological activity of an s-CPG15 protein using any of the assays described below. For example, an s-CPG15 compound may compete for and displace s-CPG15 in a receptor-binding assay.

By "s-CPG15 biological activity" is meant any one or more of the following: s-CPG15-mediated promotion of cell survival, s-CPG15-mediated promotion of neurite outgrowth, s-CPG15-mediated promotion of cell differentiation, s-CPG15-mediated reduction of cell death, s-CPG15 binding to the IR, IGF-1R, or IGF-2R, either direct binding or indirect (e.g., in conjunction with one or more co-receptors), or s-CPG15-mediated activation of the IR, IGF-1R, or IGF-2R. Activation of the IR or IGF-1R can be measured by substrate phosphorylation, phosphorylation of downstream signaling molecules (e.g., Raf1, MEK, ERK, Akt), receptor-mediated binding to substrate molecules, glucose uptake, or activation of immediate/early genes induced by insulin). Activation of IGF-2R can be measured by ligand (e.g., insulin, IGF-1, and s-CPG15) endocytosis assays as described herein or known in the art. In one embodiment, an s-CPG15 compound has the biological activity of a native CPG15 protein that has undergone all of the following modifications: 1) the signal sequence and the GPI linkage sequence have been cleaved; 2) the CPG15 protein has been bound to a cell membrane; and 3) the CPG15 protein has been released from the cell and secreted into the supernatant. The biological activity of s-CPG15 can be assayed using standard apoptotic assays or growth or differentiation assays, such as described in U.S. Patent Application Publication No. 20040176291 and PCT Publication No. WO 2004/031347, incorporated herein by reference, or by using the receptor binding assays, kinase receptor assays, glucose import assays, and insulin-induced immediate/early gene expression assays described herein or known in the art.

By "dnCPG-15" is meant any protein having substantial identity to at least a fragment of a CPG15 protein that can reduce (e.g., by at least 20%, 30%, 40%, 50%, 60%, 70%, 80%, 90%, 95% or more) or inhibit s-CPG15 biological activity. Desirably, a dnCPG15 protein will bind to but not activate the insulin-binding receptor (e.g., IR or IGF-1R). Examples of dnCPG15 include truncated forms of CPG15 (t-CPG15) that lack the amino acids encoding the GPI linkage sequence (e.g., amino acids 1-114 or 1-115 of the human CPG15 protein (SEQ ID NO: 4; GenBank Accession Number NM_016588)) and the dnCPG15 shown in FIG. 4 (SEQ ID NO: 5).

By "candidate plasticity gene 15-2" or "cpg15-2" is meant any nucleic acid sequence that encodes a protein that is substantially identical to any of the proteins set forth in SEQ ID NOs: 2 and 3 or GenBank accession numbers NM_198443 (human) or AK090312 (mouse). The term "cpg15-2" includes nucleic acid sequence encoding the membrane bound or soluble forms of any of the above proteins, or any modifications or conservative substitutions to the proteins. Exemplary cpg15-2 nucleic acid sequences include SEQ ID NO: 6 and SEQ ID NO: 7.

By "CPG15-2" is meant a protein that is substantially identical to any of the amino acid sequences set forth in SEQ ID NOs: 2 and 3 or GenBank accession numbers NM_198443 (human) or AK090312 (mouse) and includes a GPI consensus sequence and a secretion signal sequence. The term CPG15-2 includes naturally occurring forms of the protein, non-natural or synthetic forms of the protein, and any conservative substitutions or modifications as known in the art and described herein. As used herein, CPG15-2 refers to the complete, unprocessed form of the protein including the GPI consensus sequence and the secretion signal sequence, or the membrane bound form of the protein. Additional details regarding CPG15-2 can be found in U.S. Patent Application Publication No. 20050187175 or PCT Publication No. WO 2005/032476, herein incorporated by reference.

By "CPG15-2 compound" is meant any small molecule chemical compound, antibody, nucleic acid molecule, or polypeptide, or fragment thereof that is substantially identical to an CPG15-2 amino acid or nucleic acid sequence or that has substantial identity to the secondary or tertiary structure of an CPG15-2 protein, or fragments or derivatives thereof; and that has CPG15-2 biological activity, as described below. For example, an CPG15-2 compound may not have extensive primary sequence identity to CPG15-2 but its secondary structure may closely resemble the secondary structure of CPG15-2. Examples of CPG15-2 compounds include CPG15-2 polypeptides, fragments, or derivatives thereof. A preferred CPG15-2 compound is the soluble CPG15-2 polypeptide. An CPG15-2 compound may also have the ability to competitively inhibit the biological activity of an s-CPG15-2 or CPG15-2 protein using any of the assays described below. For example, an CPG15-2 compound may compete for and displace s-CPG15-2 or CPG15-2 in a receptor-binding assay.

By "soluble CPG15-2" or "s-CPG15-2" is meant any soluble form of a CPG15-2 protein described above that lacks secretion signal sequence, or lacks both the signal secretion sequence and the GPI linkage sequences, and includes an amino acid sequence that is substantially identical to either of the following core domains: SEGPNRCDTIYQGFAEC-LIRLGDGMGRGGELQTVCRSWNDF-HACASRVLSGCPEEAAAVWESLQQEAR-RAPHPDNLHILCGAPVSVRERIAGPETNQETLRATA (mouse) (SEQ ID NO: 8) and AAGPNRCDTIYQGFAEC-LIRLGDSMGRGGELETICRSWNDF-HACASQVLSGCPEEAAAVWESLQQEAR-QAPRPNNLHTLCGAPVHVRERGTGSETNQETLRATA (human) (SEQ ID NO: 9). The core domain generally refers to the domain of the protein after cleavage of the GPI linkage sequences or the secretion signal sequence, or both. For the naturally occurring forms of CPG15-2, these sequences are typically cleaved off after translation and processing of the protein. The remaining sequences after cleavage are known as the core domain. An asparagine residue (N) can also be present at the carboxy terminus of the protein. A methionine residue (M) can be inserted at the amino terminus of the core domain sequence. s-CPG15-2 can refer to the naturally occurring forms of the protein or to any non-natural or synthetic form of the protein. s-CPG15-2 can also include any conservative substitutions or modifications as known in the art and described herein.

By "s-CPG15-2 compound" is meant any small molecule chemical compound, antibody, nucleic acid molecule, or polypeptide, or fragment thereof that is substantially identical to an s-CPG15-2 amino acid or nucleic acid sequence or that has substantial identity to the secondary or tertiary structure of an s-CPG15-2 protein, or fragments or derivatives thereof, and that has CPG15-2 biological activity, as described below. For example, an s-CPG15-2 compound may not have extensive primary sequence identity to s-CPG15-2 but its secondary structure may closely resemble the secondary structure of s-CPG15-2. Examples of s-CPG15-2 compounds include s-CPG15-2 polypeptides, fragments, or derivatives thereof. A preferred s-CPG15-2 compound is the soluble CPG15-2 polypeptide. An s-CPG15-2 compound may also have the ability to competitively inhibit the biological activity of an s-CPG15-2 protein using any of the assays described below. For example, an s-CPG15-2 compound may compete for and displace s-CPG15-2 in a receptor-binding assay.

In one embodiment, a s-CPG15-2 compound has the biological activity of a native CPG15-2 protein that has undergone all of the following modifications: 1) the signal sequence and the GPI linkage sequence have been cleaved; 2) the CPG15-2 protein has been bound to a cell membrane; and 3) the CPG15-2 protein has been released from the cell into the supernatant. The biological activity of s-CPG15-2 can be assayed using standard apoptotic assays or growth or differentiation assays, such as described U.S. Patent Application Publication No. 20050187175 and PCT Publication No. WO 2005/032476, incorporated herein by reference, or by using the receptor binding assays, kinase receptor assays, glucose import assays, and insulin-induced immediate/early gene expression assays described herein or known in the art.

By "CPG15-2 biological activity" is meant any one or more of the following: CPG15-2- or s-CPG15-2-mediated promotion of cell survival, CPG15-2- or s-CPG15-2 mediated promotion of neurite outgrowth, CPG15-2- or s-CPG15-2-mediated promotion of cell differentiation, CPG15-2- or s-CPG15-2-mediated reduction of cell death, CPG15-2 or s-CPG15-2 binding to the IR, IGF-1R, or IGF-2R, either direct binding or indirect (e.g., in conjunction with one or more co-receptors), or an CPG15-2- or s-CPG15-2-mediated activation of the IR, IGF-1R, or IGF-2R. Preferably, the CPG15-2 biological activity is the biological activity of the soluble form of CPG15-2 (s-CPG15-2). Activation of the IR or IGF-1R can be measured by substrate phosphorylation, phosphorylation of downstream signaling molecules (e.g., Raf1, MEK, ERK, Akt), receptor-mediated binding to substrate molecules, glucose uptake, or insulin-induced immediate/early gene activation). Activation of IGF-2R can be measured by ligand (e.g., insulin, IGF-1, and s-CPG15) endocytosis assays as described herein or known in the art.

By "dnCPG15-2" is meant any protein having substantial identity to at least a fragment of a CPG15-2 protein that can reduce (e.g., by at least 20%, 30%, 40%, 50%, 60%, 70%, 80%, 90%, 95% or more) or inhibit s-CPG15-2 biological activity. Desirably, a dnCPG15-2 protein will bind to but not activate the IR or IGF-1R. Examples of dnCPG15-2 include truncated forms of CPG15-2 (t-CPG15-2) that lack the amino acids encoding the GPI linkage sequence.

By "cell death" is meant the process or series of events, which ultimately lead to a non-functioning, non-living cell. Cell death as used herein typically refers to apoptosis (programmed cell death) or necrosis. By "preventing or reducing" cell death is meant any treatment or therapy that causes an overall decrease in the number of cells undergoing cell death relative to a control. Preferably, the decrease will be at least 15%, 20%, 25%, 30%, 35%, 40%, 45% and most preferably at least 50%, 60%, 70%, 80%, 90% or more. By "excessive cell death" is meant an increase in the number of cells undergoing cell death as compared to a control population of cells. Preferably, excessive cell death includes an increase of 10% or more in the total number of cells undergoing cell death. More preferably the increase is 15%, 20%, 25%, 30%, 35%, and most preferably an increase of 40%, 50%, 60%, 70%, 80%, 90% or more in the total number of cells undergoing cell death as compared to a control population of cells.

By "cell survival" is meant the reversal or prevention of cell death signaling pathways or the promotion of pathways that antagonize cell death, thereby increasing the life span of a cell or the number of cells that survive in a given situation, relative to a control. By "promoting" cell survival is meant any treatment or therapy that causes an overall increase in the number of cells. Preferably, the increase will be at least 15%, 20%, 25%, 30%, 35%, 40%, 45% and most preferably at least 50%, 60%, 70%, 80%, 90% or more. "Undesirable cell survival" is characterized by an increase in cell proliferation or a decrease in cell death such that the total number of growing cells exceeds that of a normal control population. Preferably, a condition of "undesirable cell survival" is selected from a group consisting of cancer, tumor-associated angiogenesis, or autoimmune diseases. Preferably, "undesirable cell survival" refers to an increase is 15%, 20%, 25%, 30%, 35%, 40%, 45% and most preferably at least 50%, 60%, 70%, 80%, 90% or more than the number of growing cells in a control population. Preferably, changes in cell survival and cell death are measured using a standard serum starvation assay such as the one described herein below.

By "cellular proliferative disease" is meant any condition characterized by the undesired proliferation of cells. Included are conditions such as neoplasms, cancers, myeloproliferative disorders, and solid tumors. By "cancer" is meant both benign and malignant growths of cancer. The cancer can be a non-solid tumor (a tumor that grows within the blood stream) or a solid tumor, which refers to one that grows in an anatomical site outside the bloodstream. Solid tumors can be separated into those of epithelial cell origin and those of non-epithelial cell origin. Examples of epithelial cell solid tumors include tumors of the bladder, blood, breast, colon, duodenum, gall bladder, intestine, kidney, labium, liver, lung, lymph node, mouth, nasopharynx, nervous tissue, ovary, pancreatic, prostate, rectal, skeletal muscle, skin, spinal cord, spleen, stomach, testes, thymus, thyroid, trachea, urogenital tract, ureter, urethra, uterus, or vaginal cancer. Solid tumors of non-epithelial origin include sarcomas, brain tumors, and bone tumors. Desirably, the methods of the invention are used to treat a cancer that is characterized by increased IGF-1 or IGF-1 receptor expression levels or biological activity.

By "compound" is meant any small molecule, chemical compound, antibody, nucleic acid, polypeptide, or a fragment thereof.

By "decreasing" is meant the ability to cause an overall reduction, preferably of 20%, 30%, 40%, 50%, 60%, 70%, 80%, 90% or greater. For example, decreasing can refer to an overall reduction in the expression level or biological activity of the IR or IGF-1R after treatment with a compound of the invention.

By "detectable label" is meant a molecule or fragment thereof that has been derivatized with an exogenous label (e.g., an isotopic label, fluoroscein, or radiolabel) that causes the molecule or fragment thereof to have different physico-chemical properties to the naturally-occurring molecule or fragment thereof. "Detect" or "detection" refers to identifying the presence, absence, or amount of the substance or state to be detected.

By "derivative" is meant a molecule or fragment thereof that has been chemically altered from a given state. Derivitization may occur during non-natural synthesis or during later handling or processing of a molecule or fragment thereof. Derivitization may result from a natural process, such as the steps of a cellular biochemical pathway. Recombinant nucleic acids or proteins that alter the naturally-occurring nucleic acid or amino acid sequence, respectively, may also be referred to as derivatives.

By "diabetes" or "diabetes mellitus" is meant a heterogeneous clinical disorder resulting from insulin resistance or insulin deficiency that is generally divided into two main types: insulin dependent and non-insulin-dependent. Insulin-dependent diabetes mellitus (IDDM, also called Type 1 diabetes) is identified by the development of ketoacidosis in the absence of insulin therapy. Type 1 diabetes most often manifests in childhood (hence also called juvenile onset diabetes) and is the result of an autoimmune destruction of the β-cells of the pancreas. Non-insulin-dependent diabetes mellitus (NIDDM or Type 2 diabetes) is characterized by milder hyperglycemia and rarely leads to ketoacidosis. Type 2 diabetes generally manifests after age 40. Type 2 diabetes is thought to result from genetic defects that cause both insulin resistance and insulin deficiency. There are three main forms of Type 2 diabetes: late onset associated with obesity, late onset not associated with obesity, maturity onset type diabetes of the young (MODY). This form of diabetes mellitus appears to be the result of mutations in the glucokinase gene. Diabetes mellitus can also result from a variety of causes including MODY, pancreatic disease, cardiovascular disease, endocrine disease, drug-induced diabetes, type B insulin resistance, mutations in the insulin gene, mutations in the insulin receptor gene, gestational diabetes, and other genetic syndromes that have either diabetes or impaired glucose tolerance associated with them including lipoatrophic diabetes, metabolic syndrome (Syndrome X), Wolfram syndrome, Down syndrome, Klinefelter syndrome (XXY males), Turner syndrome, myotonic dystrophy, muscular dystrophy, Huntington disease, Friedrich ataxia (associated with deficiency in purine nucleotide phosphorylase), Prader-Willi syndrome, Werner syndrome, Cockayne syndrome, and others.

The terms "diagnosis" and "diagnostics" also encompass the terms "prognosis" and "prognostics," respectively, as well as the applications of such procedures over two or more time points to monitor the diagnosis and/or prognosis over time, and statistical modeling based thereupon.

By "differentiation" is meant the process during which young, immature (unspecialized) cells take on individual characteristics and reach their mature (specialized) form and function. By "promoting" cell differentiation is meant any treatment or therapy that causes an overall increase in the number of differentiated cells as measured by assays which quantitate the presence or absence of a defining characteristic of a differentiated cell. Preferably, the increase in differentiation of a cell population will be at least 15%, 20%, 25%, 30%, 35%, 40%, 45% and most preferably at least 50%. In one example, stem cell conversion to neurons can be measured by expression of neuronal markers such as neurofilament-M, Map2, and neuron specific enolase. In another example, the clonogenic Colony Assay offered by Cambrex Corporation, can be used to determine differentiation of hematopoietic progenitor cells into myeloid (CFU-GM), erythroid (CFU-E, BFU-E), megakaryocyte (CFU-Meg), and mixed (myeloid and erythroid) colonies.

By "downstream signaling molecule" is meant a molecule in the cell that is not a direct substrate of an insulin-binding receptor (e.g., IR or IGF-1R), which becomes phosphorylated following activation of the receptor. Examples of downstream signaling molecules include, but are not limited to Raf1, MEK, ERK, and Akt.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, 100, 200, 300, 400, 426 or more nucleotides or 10, 20, 30, 40, 50, 60, 70, 80, 90, 100, 120, 140, or 142 amino acids or more. Preferred fragments of s-CPG15 and s-CPG15-2 that are used as IBRAs in the methods of the invention will have s-CPG15 biological activity and may include, for example, the domain of CPG15 or CPG15-2 required for binding to an insulin-binding receptor (e.g., IR, IGF-1R, and IGF-2) or co-receptor.

By "homologous" is meant any gene or polypeptide sequence that bears at least 30% homology, more preferably 40%, 50%, 60%, 70%, 80%, and most preferably 90%, 95%, 96%, 97%, 98%, 99%, or more homology to a known gene or polypeptide sequence over the length of the comparison sequence. A "homologous" polypeptide can also have at least one biological activity of the comparison polypeptide. For polypeptides, the length of comparison sequences will generally be at least 16 amino acids, preferably at least 20 amino acids, preferably 30, 40, 50, 60, 70, 80, 90, 100, 110, 120, 130, 140, or at least 142 amino acids or more. For nucleic acids, the length of comparison sequences will generally be at least 25, 50, 100, 125, 150, 200, 250, 300, 350, 400, or at least 426 nucleotides or more. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein or polypeptide.

By "increasing" is meant the ability to cause an overall increase, preferably of 20%, 30%, 40%, 50%, 60%, 70%, 80%, 90% or greater. For example, increasing can refer to an overall elevation in the expression level or biological activity of an insulin-binding receptor after treatment with an IBRA as compared to an untreated sample.

By "inhibitor of s-CPG15" is meant any small molecule chemical compound, antibody, nucleic acid molecule, polypeptide, or fragments thereof, that can reduce (e.g., by at least 20%, 30%, 40%, 50%, 60%, 70%, 80%, 90%, 95% or more) or inhibit the expression levels or biological activity of an s-CPG15. Examples of inhibitors of s-CPG15 include dnCPG15 (e.g., SEQ ID NO: 5), dn-CPG15-2, t-CPG15 or t-CPG15-2, antibodies that specifically bind s-CPG15, and antisense nucleobase oligomers or dsRNA to CPG-15 (see for example, U.S. Patent Application Publication Nos. 20040176291 and 20050187175 and PCT Publication Nos. WO 2004/031347 and WO 2005/032476).

By "inhibitor of CPG15-2" is meant any small molecule chemical compound, antibody, nucleic acid molecule, polypeptide, or fragments thereof, that can reduce (e.g., by at least 20%, 30%, 40%, 50%, 60%, 70%, 80%, 90%, 95% or more) or inhibit the expression levels or biological activity of a CPG15-2 or s-CPG15-2 polypeptide. Examples of inhibitors of CPG15-2 include dnCPG15 (e.g., SEQ ID NO: 5), dn-CPG15-2, t-CPG15 or t-CPG15-2, antibodies that specifically binds CPG15-2 or s-CPG15-2, and antisense nucleobase oligomers or dsRNA to CPG15-2 or s-CPG15-2 (see for example, U.S. Patent Application Publication Nos. 20040176291 and 20050187175 and PCT Publication Nos. WO 2004/031347 and WO 2005/032476). One example of a preferred inhibitor of CPG15-2 is a molecule which inhibits the biological activity of an s-CPG15-2.

By "insulin-binding receptor" is meant any cellular receptor, which has the ability to bind insulin. Included within this definition are any mammalian forms of the insulin receptor, IGF-1 receptor, and IGF-2 receptor. Insulin binding may be direct or indirect (e.g., in conjunction with one or more co-receptors).

By "insulin-binding receptor activator" or "IBRA" is meant any one or more of the following: an s-CPG15 compound, an s-CPG15-2 compound, a CPG15-2 compound, a cpg15 nucleic acid molecule which encodes a CPG15 protein or cpg15-2 nucleic acid molecule which encodes a CPG15-2 protein, wherein the IBRA has the ability to bind to or activate, or both, an insulin-binding receptor (e.g., IR, IGF-1R, or IGF-2R). Methods to measure the ability of an insulin-binding activator compound to bind or activate an insulin-binding receptor are provided herein and are known in the art.

By "insulin-binding receptor inhibitor" of "IBRI" is meant an inhibitor of s-CPG15 expression levels or biological activity, an inhibitor of CPG15-2 expression levels or activity, a compound that reduces or inhibits CPG15 expression levels, or a compound that reduces or inhibitors CPG15-2 expression levels, that can reduce or inhibit the biological activity of an insulin-binding receptor (e.g., IR, IGF-1R, or IGF-2R). Examples include an inhibitor of s-CPG15 and an inhibitor of CPG15-2.

By an "insulin deficiency disorder" is meant any disorder, condition or disease that is characterized by a decrease in the expression level or biological activity of an insulin-binding receptor (e.g., IR, IGF-1R, and IGF-2R), or a nucleic acid encoding an insulin-binding receptor. Examples of insulin deficiency disorders or insulin resistance disorders include Type I or Type II diabetes; hyperglycemia; hyperinsulinemia; dyslipidemia; obesity; polycystic ovarian disease; hypertension disease; cardiovascular disease; and syndrome X; and neurological conditions such as Alzheimer's disease, diabetic neuropathy, appetite control, neurodegeneration, and learning and memory impairment.

By an "insulin excess disorder" is meant any disorder, condition, or disease that is characterized by an increase in the expression level or biological activity of insulin or an insulin-binding receptor, or a nucleic acid encoding an insulin-binding receptor. Examples of insulin excess disorders include hypoglycemia, insulinomas, insulin and hypoglycemic drug overdose, gastric dumping syndrome, congenital hyperinsulinism, and proliferative disorders, such as cancer. Methods for detecting insulin levels are well known in the art. Methods for detecting IR polypeptide levels are known in the art and can include immunoassays using antibodies directed to the IR polypeptide. IR DNA expression is often detected by Southern blotting or polymerase chain reaction (PCR), and RNA expression is often detected by northern blotting, PCR, or RNAse protection assays. Methods for detecting IR biological activity are described herein and include kinase assays to detect autophosphorylation or phosphorylation of IR substrates or downstream signaling molecules, such as IRS, PI3K, or ERK.

By "insulin-induced immediate/early gene expression" is meant a number of genes that are activated within a cell expressing an insulin-binding receptor, following exposure to the cell to insulin or IGF-1 (e.g., c-fos, egr-1, pip92, c-myc, c-jun, jun-B, and fra-1). Assays to determine the insulin-induced immediate/early gene expression in a cell exposed to insulin or IGF-1 are known in the art and described herein.

By "insulin-like growth factor" (IGF) is meant a polypeptide, or a nucleic acid sequence that encodes it, or fragments or derivatives thereof, that is substantially identical or homologous to insulin-like growth factor 1 (IGF-1) or insulin like growth factor 2 (IGF-2) from any species, including bovine, ovine, porcine, equine, and human. IGF can be in a natural, synthetic, or recombinant form. IGF-1 is described in detail in U.S. Patent Application Publication No. 20050282812, herein incorporated by reference. In preferred embodiments of the invention, the IGF is IGF-1. Exemplary GenBank Accession numbers of IGF-1 sequences include NP_000609 (human), NP_034642 (mouse), NP_999421 (pig), and AAA41215 (rat).

By an "IGF-1 deficiency disorder" is meant any disorder, condition, or disease that is characterized by a decrease in the expression level or biological activity of an insulin-binding receptor (e.g., IR, IGF-1R, and IGF-2R) or a nucleic acid encoding an insulin-binding receptor. Examples of IGF-1 deficiency or resistance disorders include amyotrophic lateral sclerosis (ALS), diabetic motor neuropathy, osteoporosis, immune modulation disorders, nephrotic syndrome, small stature, and decreased muscle mass.

By "insulin-like growth factor receptor (IGF-1R)" or is meant a polypeptide, or a nucleic acid sequence that encodes it, or fragments or derivatives thereof, that is substantially identical or homologous to the insulin-like growth factor receptor 1 IGFR 1 and has IGFR 1 biological activity. In preferred embodiments of the invention, the IGFR is IGF-1R. Exemplary GenBank Accession numbers of IGF-1R sequences include AAP03720 (rat), NP_000866 and P08069 (human), and NP_034643 (mouse).

By "insulin-like growth factor receptor-1 biological activity" is meant any biological activity associated with the active form of the IGF-1 receptor. In one example, the biological activity is associated with the form of the IGF-1 receptor that is bound by a ligand, such as, insulin or IGF. IGF-1R biological activity includes stimulation of cell differentiation or proliferation, binding to substrate or effector molecules that have an SH2 domain, phosphorylation of substrate or downstream signaling molecules (e.g., ERK, IRS1, IRS2, IRS3, IRS4, PI3K, and the SH2 domain containing proteins, Akt), glucose uptake, and insulin-induced immediate/early gene expression.

By an "IGF-1 excess disorder" is meant any disorder, condition or disease that is characterized by an increase in the expression level or biological activity of IGF-1 or the IGF-1R, or a nucleic acid encoding IGF-1 or the IGF-1R. Examples of IGF-1 excess disorders include cellular proliferative disorders, cancer, acromegaly, gigantism, psoriasis, atherosclerosis, smooth muscle restenosis, and diabetes. Methods for detecting IGF-1 or IGF-1R levels are well known in the art and can include immunoassays using antibodies directed to the IGF-1 or IGF-1R polypeptide. IGF-1 or IGF-1R DNA expression is often detected by Southern blotting or polymerase chain reaction (PCR), and RNA expression is often detected by northern blotting, PCR, or RNAse protection assays. Methods for detecting IGF-1R biological activity are described herein and include kinase assays to detect phosphorylation of IGF-1R substrates or downstream signaling molecules known in the art, such as IRS ERK, or Akt.

By an "IGF-1 resistance disorder" is meant any disorder, condition, or disease that is characterized by a decreased capacity of IGF-1 to regulate metabolic or proliferative pathways. Examples of IGF-1 deficiency or resistance disorders include amyotrophic lateral sclerosis (ALS), diabetic motor neuropathy, osteoporosis, immune modulation disorders, nephrotic syndrome, small stature, and decreased muscle mass. Methods for detecting IGF-1 or IGF-1R levels are well known in the art, and are described herein.

By "insulin-like growth factor-2 receptor biological activity" is meant any biological activity associated with the active form of the IGF-2 receptor. In one example, the biological activity is associated with the form of the IGF-1 receptor that is bound by a ligand, such as insulin or IGF. In one example, the IGF-2R biological activity is the internalization of the bound ligand (e.g., insulin, IGF-1, s-CPG15, or s-CPG15-2) via receptor-mediated endocytosis.

By "insulin receptor biological activity" is meant any biological activity associated with the active form of the insulin receptor or with insulin when bound to the IR. Examples include binding to substrate or effector molecules that have an SH2 domain, phosphorylation of substrate molecules or downstream signaling molecules (e.g., ERK, IRS1, IRS2, IRS3, IRS4, PI3K, and the SH2 domain containing proteins, Akt), glucose-uptake, and insulin-induced immediate/early gene expression (e.g., c-fos, egr-1, pip92, c-myc, c-jun, jun-B, and fra-1).

By an "insulin resistance disorder" is meant any disorder, condition, or disease that is characterized by a decreased capacity of circulating insulin to regulate glucose uptake and nutrient metabolism. Insulin resistance occurs when the normal amount of insulin secreted by the pancreas is not able bind to the insulin receptor and allow the glucose to pass from the blood into the cell. Examples of insulin deficiency disorders or insulin resistance disorders include Type I or Type II diabetes; hyperglycemia; hyperinsulinemia; dyslipidemia; obesity; polycystic ovarian disease; hypertension disease; cardiovascular disease; and syndrome X; and neurological conditions such as Alzheimer's disease, diabetic neuropathy, appetite control, neurodegeneration, and learning and memory impairment. Methods for detecting insulin levels are well known in the art. Methods for measuring insulin activity can include activation of the IR and assays for measuring blood glucose levels. Methods for detecting IR polypeptide levels can include immunoassays using antibodies directed to the IR polypeptide. IR DNA expression is often detected by Southern blotting or polymerase chain reaction (PCR), and RNA expression is often detected by northern blotting, PCR, or RNAse protection assays. Methods for detecting IR biological activity are described herein and include kinase assays to detect autophosphorylation or phosphorylation of IR substrates or downstream signaling molecules, are known in the art, such as PI3K, ERK, or Akt.

By "kinase activity" is meant the ability to catalyze the transfer of a phosphate group from adenosine triphosphate (ATP) to a residue (e.g., tyrosine, threonine, serine) on a substrate polypeptide or protein.

By "membrane component" is a meant any lipid (e.g., cholesterol), glycolipid, protein, phospholipid, lipoprotein, liposaccharide, or phosphoprotein that is naturally occurring in a cellular membrane.

By "necrosis" or "necrotic cell death" is meant cell death associated with a passive process involving loss of integrity of the plasma membrane and subsequent swelling, followed by lysis of the cell.

By "neurological condition" is meant any condition of the central or peripheral nervous system that is associated with neuron degeneration or damage. Examples of neurological conditions treatable by the methods of the invention include neurological conditions associated with aberrant insulin or IGF-1 signaling and neurological conditions that involve inappropriate cell death.

By "neurite outgrowth" is meant the process by which a neuron extends new cellular processes (i.e. neurites) from the cell body. Neurite outgrowth includes both the formation of new neurites or an increase in the length, or new branches additions to pre-existing neurites. Neurites refer to both axonal and dendritic processes and processes of mixed identity.

By "normal range of blood glucose" is meant 70 to 99 mg/dl for a fasting blood glucose level. A person with a fasting blood glucose level between 100 to 125 mg/dl has pre-diabetes. A person with a fasting blood glucose level of 126 mg/dl or higher on more than one testing occasion has diabetes. It should be noted that blood glucose levels can fluctuate in healthy subjects and sometimes the presence of symptoms associated with hypo- or hyperglycemia are used to determine if the blood glucose levels are within a normal range. Assays used to determine blood glucose levels include the Fasting Plasma Glucose Test (FPG) and the Oral Glucose Tolerance Test (OGTT).

By "operably linked" is meant that a gene and a regulatory sequence(s) are connected in such a way as to permit gene expression when the appropriate molecules (e.g., transcriptional activator proteins) are bound to the regulatory sequence(s).

By "purified" is meant is at least 60%, by weight, free from proteins and other molecules (e.g., naturally occurring or synthetic) with which it is naturally associated. Preferably, the preparation is at least 75%, more preferably 90%, and most preferably at least 99% purified, by weight.

By "receptor substrate molecule" is meant any protein that can bind to or act as a downstream effector protein for a receptor. Desirably, the receptor substrate molecule is a protein that can bind to the IR or IGF-1R or that is phosphorylated by the IR or IGF-1R. Examples include IRS1, IRS2, IRS3, IRS4, PI3K, Shc, Grb2, and any SH2 domain containing protein that can bind to a phosphorylated tyrosine in the receptor. It should be noted that some receptor substrate molecules may not directly bind the receptor but may act as a substrate through an adaptor molecule which binds both the substrate and the receptor. A number of other downstream signaling molecules become phosphorylated (via activated G-proteins) following IR or IGF-1R activation, including, for example, ERK.

By "small interfering RNAs (siRNAs)" is meant an isolated dsRNA molecule, preferably greater than 10 nucleotides in length, more preferably greater than 15 nucleotides in length, and most preferably 19 nucleotides or more in length, that is used to identify the target gene or mRNA to be degraded. A range of 19-25 nucleotides is the most preferred size for siRNAs, but they can be as long as 30, 40, 50, 60, 70 or more nucleotides in length. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nucleotide RNA or internally (at one or more nucleotides of the RNA). In a preferred embodiment, the RNA molecules contain a 3'-hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNAi. As used herein "mediate RNAi" refers to the ability to distinguish or identify which RNAs are to be degraded.

By "specifically binds" is meant an antibody or antigen binding fragment thereof that recognizes and binds an antigen but that does not substantially recognize or bind to other molecules in a sample, e.g., a biological sample, that naturally includes protein. Specific recognition of an antigen by an antibody can be assayed using standard art known techniques such as immunoprecipitation, western blotting, and ELISA.

A "subject" for the purposes of the present invention includes humans and other animals, preferably warm-blooded mammals including mice, rats, guinea pigs, hamsters, rabbits, cats, dogs, goats, sheep, cows, or monkeys. Thus, the methods are applicable to both human therapy and veterinary applications.

By "substantially identical" is meant a nucleic acid, protein, or amino acid sequence that shares at least 60%, 65%, 70%, 75%, 80%, 85%, 90%, 95%, 96%, 97%, 98%, 99%, or 100% sequence identity with another nucleic acid, protein or amino acid sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith and Waterman, *J. Mol. Biol.* 147:195-7, 1981); "BestFit" (Smith and Waterman, *Adv. Appl. Math.* 2:482-489, 1981) as incorporated into GeneMatcher Plus™; Schwarz and Dayhof, "Atlas of Protein Sequence and Structure," Dayhof, M. O., Ed pp 353-358, 1979; BLAST program (Basic Local Alignment Search Tool); Altschul et al., *J. Mol. Biol.* 215: 403-410, 1990); BLAST-2; BLAST-P; BLAST-N; BLAST-X; WU-BLAST-2; ALIGN; ALIGN-2; CLUSTAL; or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 10 amino acids, preferably 20, 30, 40, 50, 60, 70, 80, 90, 100, 110, 120, 130, or at least 142 amino acids or more, up to the full length of the protein. For nucleic acids, the length of comparison sequences will generally be at least 25, 50, 100, 125, 150, 200, 250, 300, 350, 400, or at least 426 nucleotides or more, up to the full length of the protein. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "treating" is meant administering a compound or a pharmaceutical composition for prophylactic and/or therapeutic purposes. To "treat disease" or use for "therapeutic treatment" refers to administering treatment to a subject already suffering from a condition to improve the subject's condition or to prevent, reduce, or eliminate the symptoms of the disease in the subject. Preferably, the subject is diagnosed as suffering from a condition based on identification of any of the characteristic symptoms known for that condition. To "prevent disease" refers to prophylactic treatment of a subject who is not yet ill, but who is susceptible to, or otherwise at risk of, developing a particular condition. Thus, in the claims and embodiments, treating is the administration to a subject either for therapeutic or prophylactic purposes.

Other features and advantages of the invention will be apparent from the following description of the preferred embodiments thereof, and from the claims.

BRIEF DESCRIPTION OF THE DRAWINGS

FIGS. 1A-1B show the effects of s-CPG15 and dnCPG15 on the growth factor mediated rescue of cortical neurons from starvation induced apoptosis. FIG. 1A is a graph showing the rescue of primary cortical neurons undergoing apoptosis induced by growth factor deprivation by the addition of different growth factors (15, s-CPG15; I, Insulin; IGF-1; B, BDNF; NT-3) but not by the addition of NGF. (*P<0.001). FIG. 1B is a graph showing that a dominant negative form of CPG15 (dnCPG15) can block the rescue by s-CPG15, insulin and IGF-1. dnCPG15 had no effect on BDNF or NT-3 induced rescue. (*P<0.001)

FIGS. 3A-3C show the activation of the PI3K/Akt and ERK pathways by s-CPG15. FIG. 3A shows a western blot that demonstrates that s-CPG15 stimulates the phosphorylation of ERK1/2. Primary cortical neurons cultured for 6 days were stimulated for 10 minutes with s-CPG15 or insulin and analyzed by immunoblotting for the activation of ERK1/2, using phosphorylation-specific ERK1/2 (pERK1/2) antibodies. An antibody against ERK1/2 was used as loading control. FIG. 3B shows a graph which depicts the fold increase in ERK phosphorylation after the addition of s-CGP15 or insulin. FIG. 3C shows two graphs which demonstrate that neuronal survival depends on PI3K, but not on MEK activation. After 6 DIV neurons were incubated with a PI3K inhibitor (LY294002) or a MEK inhibitor (U0126) during the 12 hour starvation period. Neurons were stained with Hoechst and apoptotic nuclei were counted.

FIG. 4A shows the amino acid sequence for human CPG15 (SEQ ID NO: 4). FIG. 4B shows the amino acid sequence for a dominant negative CPG15 (SEQ ID NO: 5).

FIG. 5A shows the DNA sequence (SEQ ID NO: 6) with the predicted amino acid translation of human cpg15-2 (SEQ ID NO: 2). FIG. 5B shows the DNA sequence (SEQ ID NO: 7) with the predicted amino acid translation of mouse cpg15-2 (SEQ ID NO: 3).

FIG. 6 shows the amino acid sequence for mouse CPG15 (SEQ ID NO: 10).

DETAILED DESCRIPTION

Figure 2:
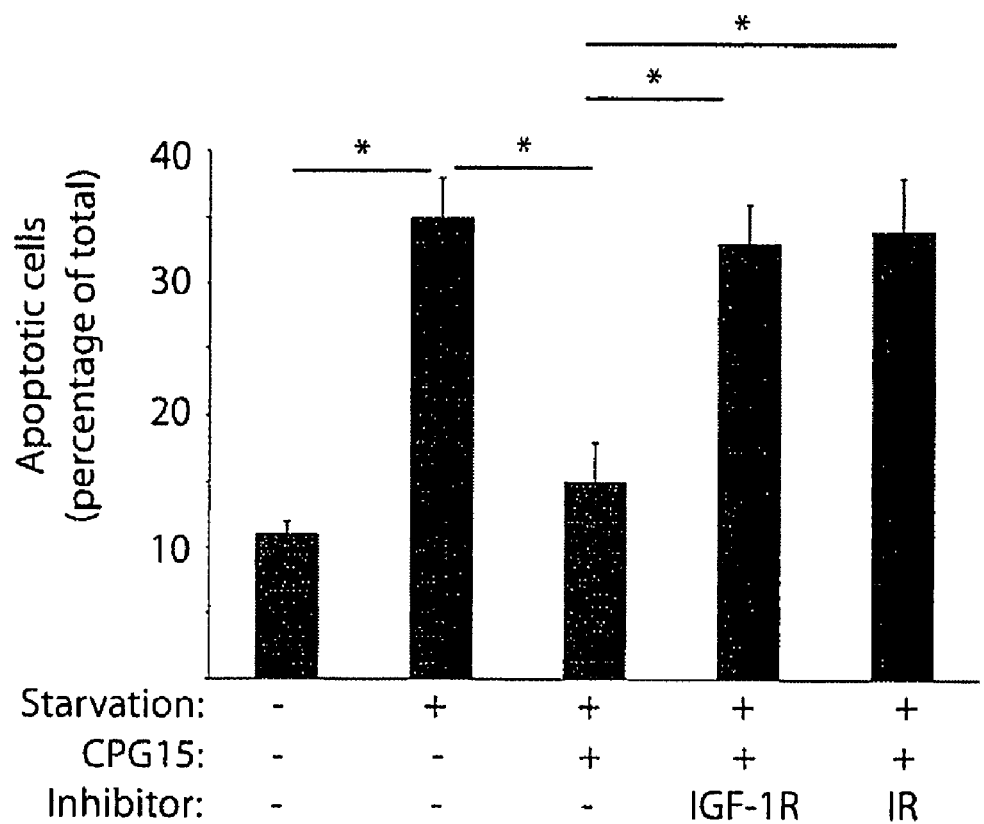
FIG. 2 is a graph showing the rescue effect of s-CPG15 can be prevented by inhibitors for the IGF-1- and insulin-receptor. Primary cortical neurons undergoing apoptosis induced by growth factor deprivation were incubated with s-CPG15 alone or in combination with an IGF-1 receptor blocking AB (IGF-1R AB) or with HNMPA, a specific inhibitor of the insulin receptor. While s-CPG15 alone can rescue neurons from starvation-induced apoptosis, this effect was blocked by the IGF-1R blocking AB and the insulin receptor inhibitor. (*P<0.001).

Insulin and IGF work through their cognate receptors, IR and IGF-1R, respectively, to regulate a variety of metabolic and proliferative signaling pathways. The insulin and IGF-1 receptors are tyrosine kinase receptors that can autophosphorylate and phosphorylate effector molecules such as insulin receptor substrates (IRS) including IRS1, IRS2, IRS3, and IRS4. Once phosphorylated, the IRS proteins can activate multiple effector pathways include the PI3K pathway, ERK cascade, Akt pathway, and others. These pathways then function to regulate a variety of cellular processes including cellular growth and survival, gene transcription, apoptosis, metabolism, and cellular proliferation. Aberrant signaling from either or both of these receptors can lead to a variety of disorders including diabetes, obesity, disorders relating to appetite control, cancer, neurological conditions, learning and memory impairment, reproductive disorders, growth disorders, such as small stature and gigantism, and kidney disorders such as acromegaly.

We have previously described the discovery of s-CPG15, a soluble form of CPG15, and CPG15-2, a functional homolog of CPG15 which also has a soluble form (s-CPG15-2). Both s-CPG15 and s-CPG15-2 can promote cell survival in hippocampal and cortical neurons and are the subject matter of the U.S. Patent Application Publication Nos. 20040176291 and 20050187175 and PCT Publications Nos. WO 2004/031347 and WO 2005/032476, each of which is herein incorporated by reference. We have now discovered that s-CPG15, a soluble protein known to promote cell survival and differentiation, can bind to and activate the insulin receptor and the IGF-1 receptor. Binding can take place at each receptor individually, at both receptors simultaneously, or at a heterodimer composed of each receptor. Furthermore, a dominant negative form of s-CPG15 can inhibit signaling from either or both of these receptors. Therefore, s-CPG15, s-CPG15-2, and CPG15-2 compounds and inhibitors of s-CPG15 or CPG15-2 (including inhibitors of s-CPG15-2), and inhibitors of CPG15 or CPG15-2 expression can be used as agonists and antagonists to mediate signaling from either or both of these receptors, particularly for the treatment or prevention of any disease associated with aberrant signaling by either or both of these receptors.

Preparation of IBRAs

IBRAs of the invention include any s-CPG15, s-CPG15-2, or CPG15-2 compounds that can bind to or activate, or both, an insulin-binding receptor (e.g., IR, IGF-1R, or IGF-2R). s-CPG15 and s-CPG15-2 compounds include any synthetic or natural polypeptide or small molecule compound that is substantially identical to the full-length CPG15 or CPG15-2 sequences after processing (GenBank accession numbers provided above), and results in a soluble form of the protein and has s-CPG15 or CPG15-2 biological activity. Methods for the preparation and purification of s-CPG15 or s-CPG15-2 is described in U.S. Patent Application Publication Nos. 20040176291 and 20050187175 and PCT Publications Nos. WO 2004/031347 and WO 2005/032476. Soluble CPG15 (s-CPG15) does not refer to the previously reported membrane bound CPG15, the full-length, unprocessed CPG15, or the truncated form of CPG15. Analogs or homologs of s-CPG15, which retain the biological activity of s-CPG15, are also included and can be constructed, for example, by making various substitutions of residues or sequences, deleting terminal or internal residues or sequences not needed for biological activity, or adding terminal or internal residues which may enhance biological activity. Amino acid substitutions, deletions, additions, or mutations can be made to improve expression, stability, or solubility of the protein in the various expression systems. Generally, substitutions are made conservatively and take into consideration the effect on biological activity. Mutations, deletions, or additions in nucleotide sequences constructed for expression of analog proteins or fragments thereof must, of course, preserve the reading frame of the coding sequences and preferably will not create complementary regions that could hybridize to produce secondary mRNA structures such as loops or hairpins which would adversely affect translation of the mRNA.

s-CPG15, s-CPG15-2, and CPG15-2 compounds can also include any modified forms. Examples of post-translational modifications include but are not limited to phosphorylation, glycosylation, hydroxylation, sulfation, acetylation, isoprenylation, proline isomerization, subunit dimerization or multimerization, and cross-linking or attachment to any other proteins, or fragments thereof, or membrane components, or fragments thereof (e.g., cleavage of the protein from the membrane with a membrane lipid component attached). Modifications that provide additional advantages such as increased affinity, decreased off-rate, solubility, stability and in vivo or in vitro circulating time of the polypeptide, or decreased immunogenicity and include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. See, for instance, Creighton, "Proteins: Structures and Molecular Properties," 2d Ed., W. H. Freeman and Co., N.Y., 1992; "Postranslational Covalent Modification of Proteins," Johnson, ed., Academic Press, New York, 1983; Seifter et al., *Meth. Enzymol.* 182:626-646, 1990; and Rattan et al., *Ann. N.Y. Acad. Sci.* 663:48-62, 1992. Additionally, the s-CPG15 compound may contain one or more non-classical amino acids. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue.

As described above, the invention also includes chemically modified derivatives of s-CPG15, s-CG15-2, and CPG15-2 compounds, which may provide additional advantages such as increased solubility, stability and circulating time of the polypeptide, or decreased immunogenicity (see U.S. Pat. No. 4,179,337). The chemical moieties for derivitization may be selected from water soluble polymers such as, for example, polyethylene glycol, ethylene glycol/propylene glycol copolymers, carboxymethylcellulose, dextran, polyvinyl alcohol and the like. The s-CPG15 or s-CPG15-2 compound may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999; the disclosures of each of which are incorporated by reference.

The s-CPG15, s-CPG15-2, and CPG15-2 compounds may also be modified with a detectable label or by conjugation to another protein or therapeutic compound.

The biological activity of an IBRA (e.g., s-CPG15, s-CPG15-2, and CPG15-2 compounds) can be determined, for example, by cell growth or cell death assays such as the serum starvation assays, as described in U.S. Patent Application Publication Nos. US 20040176291 and US 20050187175, and PCT Publications Nos. WO 2004/031347 and WO 2005/032476, or in receptor binding assays as described herein. The s-CPG15 compound is preferably produced and/or purified by any of the methods described in U.S. Patent Application Publication Nos. 20040176291 and 20050187175, and PCT Publication Nos. WO 2004/031347 and WO 2005/032476.

Insulin

Insulin is a polypeptide hormone synthesized within the beta cells (β-cells) of the Islets of Langerhans in the pancreas. Insulin is produced as a prohormone molecule, proinsulin, that is transformed by proteolytic action into the active hormone. The actions of insulin on the metabolic pathways include control of cellular intake of certain substances, most prominently glucose in muscle and adipose tissue; increase of DNA replication and protein synthesis via control of amino acid uptake; and modification of the activity of numerous enzymes.

Insulin increases glycogen synthesis by stimulating the enzymatic action of glycogen synthase in hepatocytes and causing the storage of glucose as glycogen in the liver and muscle. When blood glucose levels fall, insulin secretion is reduced and glycogen synthesis stops. Eventually, the liver cells convert glycogen to glucose and excrete it into the blood. If blood glucose levels drop below physiologic levels, especially to dangerously low levels, release of hyperglycemic hormones forces release of glucose into the blood.

Insulin also functions in additional metabolic pathways including fatty acid synthesis by forcing fat cells to uptake glucose which in turn is converted to triglycerides; fatty acid esterification by forcing adipose tissue to make fats (i.e., triglycerides) from fatty acid esters; decreasing proteolysis by forcing reduction of protein degradation; decreasing lipolysis by forcing a reduction in the conversion of fat cell lipid stores into blood fatty acids; decreasing gluconeogenesis by forcing a decrease in the production of glucose from various substrates in liver; increasing amino acid uptake by forcing cells to absorb circulating amino acids; increasing potassium uptake by forcing cells to absorb serum potassium; and increasing arterial muscle tone by forcing the arterial wall muscle to relax, thereby increasing blood flow. Of course, a lack of insulin results in a reversal of these actions, and ultimately leads to an increase in glucose production from the liver and elsewhere.

Insulin-Like Growth Factor (IGF-1)

The insulin-like growth factors (IGFs) are polypeptides with high sequence similarity to insulin. Both insulin and IGF-1 are expressed as precursor proteins comprising, among other regions, contiguous A, B, and C peptide regions, with the C peptide being an intervening peptide connecting the A and B peptides. A mature insulin molecule is composed of the A and B chains connected by disulfide bonds, where the connecting C peptide has been removed during post-translational processing. IGF-1 retains its smaller C-peptide as well as a small D extension at the C-terminal end of the A chain, making the mature IGF-1 slightly larger than insulin. The C region of human IGF-1 appears to be required for high affinity binding to IGF-R (Pietrzkowski et al., *Cancer Res.* 52:6447-51, 1999). A further distinction between the two hormones is that, unlike insulin, IGF-1 has very weak self-association and does not hexamerize.

IGFs are part of a complex system that cells use to communicate with their physiologic environment. This complex system, known as the IGF axis, consists of two cell-surface receptors (IGF1R and IGF2R), two ligands (IGF-1 and IGF2), a family of six high-affinity IGF binding proteins (IGFBP 1-6), as well as associated IGFBP degrading enzymes, referred to collectively as proteases. The IGF axis is important for both the regulation of normal physiology, as well as a number of pathological states, including cancer. The IGF axis has been shown to play roles in the promotion of cell proliferation and the inhibition of cell death (apoptosis). IGF-2 is thought to be a primary growth factor required for early development while IGF-1 expression is seen in later development.

Insulin-like growth factor 1 (IGF-1) is mainly secreted by the liver as a result of stimulation by growth hormone (hGH). IGF-1 strongly binds to and activates the IGF-1 receptor, with weaker binding and activation occurring through insulin receptors. Almost every cell in the human body is affected by IGF-1, especially cells in muscle, cartilage, bone, liver, kidney, nerves, skin, and lungs. In addition to the insulin-like effects on metabolic pathways, IGF-1 can also regulate cell growth and development, especially in nerve cells, as well as cellular DNA synthesis. Studies of recent interest show that the IGF-1 plays an important role in aging and longevity. Nematodes, fruit-flies, and other organisms have an increased life span when the gene equivalent to the mammalian IGF is knocked out. Other studies are beginning to uncover the important role the IGFs play in diseases such as cancer and diabetes, showing for instance that IGF-1 stimulates growth of both prostate and breast cancer cells.

Clinically, recombinant human IGF-1 has been investigated for the treatment of several diseases, including Type I diabetes, amyotropic lateral sclerosis (La et al., *Neurology* 49:1621-1630, 1997), and diabetic motor neuropathy (Apfel and Kessler, *CIBA Found. Symp.* 196:98-108, 1996). Other potential therapeutic applications of IGF-1, such as osteoporosis (Canalis, *Bone* 21:215-216, 1997), immune modulation (Clark, *Endocr. Rev.* 18:157-179, 1997) and nephrotic syndrome (Feld and Hirshberg, *Pediatr. Nephrol.* 10:355-358, 1996), are also under investigation. Interestingly, several reports have shown that IGF-1 promotes the growth of normal and cancerous prostate cells both in vitro and in vivo (Angelloz-Nicoud and Binoux, *Endocrinology*

136:5485-5492, 1995; Figueroa et al., *J. Clin. Endocrinol. Metab.* 80:3476-3482, 1995; Torring et al., *J. Urol.* 158:222-227, 1997). Additionally, elevated serum IGF-1 levels correlate with increased risks of prostate cancer, and may be an earlier predictor of cancer than is prostate-specific antigen (PSA) (Chan et al., *Science* 279:563-566, 1998). Recent studies have indicated a connection between IGF-1 levels and other cancers such as breast, prostate, lung, colorectal, and ovarian. Serum IGF-1 levels are regulated by the presence of IGF binding proteins (IGFBP) which bind to IGF-1 and prevent its interaction with the IGF-1 receptor (IGF-1R; reviewed in Conover, Endocr. J. 43S:S43-S48, 1996; and Rajaram et al., *Endocr. Rev.* 18:801831, 1997). IGF-1 has also been implicated as a possible neuroprotective agent, for example in fighting the adverse effects of amyotrophic lateral sclerosis (ALS). Clearly, regulation of IGF-1R activity can play an important role in several disease states, indicating that there are potential clinical applications for both IGF-1 agonists and antagonists.

Insulin Receptor

The insulin receptor (IR) is a glycoprotein having molecular weight of 350-400 kDa (depending of the level of glycosylation). It is synthesized as a single polypeptide chain and proteolytically cleaved to yield a disulfide-linked monomer α-β insulin receptor. Two α-β monomers are linked by disulfide bonds between the α-subunits to form a dimeric form of the receptor (β-α-α-β type configuration). The α subunit is comprised of 723 amino acids, and it can be divided into two large homologous domains, L1 (amino acids 1-155) and L2 (amino acids 313-468), separated by a cysteine rich region (amino acids 156-312). Many determinants of insulin binding seem to reside in the α-subunit. The β-subunit of the insulin receptor has 620 amino acid residues and three domains: extracellular, transmembrane, and cytosolic. The extracellular domain is linked by disulfide bridges to the α-subunit. The cytosolic domain includes the tyrosine kinase domain, the three-dimensional structure of which has been solved. A unique feature of the IR is that it is dimeric in the absence of ligand.

Like the receptors for other growth factors and cytokines, the IR has an extracellular domain that binds insulin and IGF-1. During binding the intracellular tyrosine kinase is activated and mediates phosphorylation of the IRS proteins on multiple tyrosine residues; other receptors, including those for insulin-like growth factor (IGF) and various interleukins, also promote tyrosine phosphorylation of IRS proteins. Tyrosine phosphorylation sites in the IRS proteins interact with the Src-homology 2 (SH2) domains in various signaling proteins. The binding of SH2-domain containing proteins to IRS proteins initiates cascades of signals that mediate the insulin response, leading to an increase in glucose transporter molecules in the outer membrane of muscle cells and adipocytes, and therefore to an increase in the uptake of glucose from blood into muscle and adipose tissue.

During association with IRS1 or IRS2, PI3-kinase is activated and its phospholipid products activate various serine kinases and recruit them to the plasma membrane. One of these kinases, PKB/AKT, activates additional kinases that promote multiple biological responses, including glucose transport, protein and glycogen synthesis, and cellular proliferation and survival. In addition to the PI3-kinase cascade, IRS proteins engage Grb-2 to stimulate the Ras pathway and activate the mitogen-activated protein kinase cascade. The binding of SHP2 generates a complicated response, including feedback inhibition by dephosphorylation of the IRS protein. Finally, the insulin response is fine-tuned by the action of protein-tyrosine phosphatases and various serine kinases that alter the activity of the insulin receptor and the IRS proteins. When the relation between these signaling pathways is disrupted, insulin resistance occurs and contributes to the onset of glucose intolerance, obesity, and diabetes.

Insulin-Like Growth Factor Receptor (IGF-1R)

The sequence of IR is highly homologous to the sequence of IGF-1R. The sequence identity level varies from about 40% to 70%, depending on the position within the α-subunit. However, despite their similarities, insulin and IGF-1 bind only weakly to each other's receptor. The affinity of each peptide for the non-cognate receptor is about 3 orders of magnitude lower than that for the cognate receptor. In addition, IGF-1R and IR serve different physiological functions. The IR is primarily involved in metabolic functions whereas IGF-1R mediates growth and differentiation. However, both insulin and IGF-1 can induce similar mitogenic and metabolic effects. Whether each ligand elicits both activities via its own receptor, or whether insulin exerts its mitogenic effects through its weak affinity binding to IGF-1R, and IGF-1 its metabolic effects through IR, remains controversial (De Meyts, *Horm. Res.* 42:152-169, 1994).

Assays for Insulin/IR and IGF-1/IGF-1R Activity and Signaling

Assays for insulin/IR and IGF-1/IGF-1R activity are known in the art and include ligand receptor binding assays; kinase assays for tyrosine phosphorylation of the receptor (autophosphorylation) or of a receptor substrate molecule; recruitment and binding of effector molecules, adaptor proteins, or secondary messengers; phosphorylation of downstream signaling molecules; glucose uptake assays; insulin-induced immediate/early gene expression; IR or IGF-1R ELISA assays (see, for example, U.S. Pat. No. 6,987,113); and the cell death, cell survival and proliferation and cell differentiation assays as described in U.S. Patent Application Publication Nos. 20040176291 and 20050187175, and PCT Publication Nos. WO 2004/031347 and WO 2005/032476. Glucose uptake assays can be performed as is known in the art (Harmon et al., *Am. J. Physiol. Endocrinol. Metab.* 287:E758-E766, 2004). Methods to measure insulin-induced immediate/early gene expression are known in the art. For example, the expression the c-fos (an insulin-induced immediate/early gene) can be monitored by RT-PCR (Entingh et al., *J. Biol. Chem.* 278:33377-33383, 2003).

A cell or subject treated with an IBRA will display IR or IGF-1R activity that is at least 10%, 20%, 30%, 40%, 50%, 60%, 70%, 80%, 90%, or greater than the activity levels in a cell or subject where no IBRA is provided, as measured using any method known in the art or described herein. Likewise, a cell or subject treated with an IBRI (e.g., an inhibitor of s-CPG15 or CPG15-2) that acts as an antagonist on the IR or IGF-1R will display IR or IGF-1R activity that is at least 10%, 20%, 30%, 40%, 50%, 60%, 70%, 80%, 90%, or 100% reduced as compared to the activity levels in a cell or subject where the IBRI is not added or a natural ligand (e.g., insulin or IGF-1) or an insulin-binding receptor agonist is added, as measured using any method known in the art or described herein.

Assays for IGF-2R Activity

Assays for IGF-2R activity are known in the art and include ligand internalization (e.g., endocytosis) assays. Methods for ligand endocytosis assays are described in the art, and may include assays that measure the endocytosis of labeled ligand (e.g., radionuclide labeled) (Authier et al., *Biochem. J.* 332:421-430, 1998).

A cell or subject treated with an IBRA will display IGF-2R activity that is at least 10%, 20%, 30%, 40%, 50%, 60%, 70%, 80%, 90%, or greater than the activity levels in a cell or subject where no IBRA is provided, as measured using any method known in the art or described herein. Likewise, a cell or subject treated with an IBRI (e.g., an inhibitor of s-CPG15 or CPG15-2) that acts as an antagonist on the IGF-2R will display IGF-2R activity that is at least 10%, 20%, 30%, 40%, 50%, 60%, 70%, 80%, 90%, or 100% reduced as compared to the activity levels in a cell or subject where the IBRI is not added or a natural ligand (e.g., insulin or IGF-1) or an insulin-binding receptor agonist is added, as measured using any method known in the art or described herein.

Therapeutic Uses of the Invention

We have discovered that s-CPG15 can bind to and activate signaling from the IR or the IGF-1R or both. We have also discovered that inhibitors of s-CPG15, such as a dominant negative CPG15, can block the function of the insulin and IGF-1 receptors.

The binding of insulin to IR or of IGF-1 to IGF-1R activates the tyrosine kinase domains of these receptors, which in turn leads to the phosphorylation of various intracellular substrates including the insulin receptor substrate-1 (IRS-1, IRS-2, IRS-3, and IRS-4), phospatidylinositol 3-kinase (PI3K) and extracellular signal-regulated kinase (ERK) that activate signaling pathways such as the mitogen-activated protein kinase (MAPK) and the PI3K/Akt pathways. The activation of MAPK and the PI3K/Akt pathways can affect a variety of cellular functions including cell growth and survival, specifically neuronal survival, apoptosis, metabolism, gene transcription, proliferation, differentiation, and metabolism. Therefore activation or inhibition of signaling pathways by these receptors has a primary role in the onset or progression of a number of pathological conditions associated with these cellular functions. Examples include diabetes, obesity, disorders relating to appetite control, cancer, neurological conditions, learning and memory impairment, reproductive disorders, growth disorders, such as small stature and gigantism, and kidney disorders such as acromegaly.

The therapeutic applications for the use of an IBRA (e.g., s-CPG15, s-CPG15-2, or CPG15-2 compounds) or the use of IBRIs (e.g., inhibitors of s-CPG15, inhibitors of s-CPG15-2, and inhibitors of CPG15 or CPG15-2 expression) for the treatment or prevention of any disease associated with aberrant insulin/IR or IGF-1/IGF-1R expression, activity, or both are described below. The various disorders that can be treated or prevented using the compounds and methods of the invention are described below. It should be noted that IBRIs may inhibit signaling from either the IR or the IGF-1R or both simultaneously or independently.

Disorders generally affecting the insulin receptor can be divided into five general categories:

(1) Disorders involving receptor regulation. This category includes disorders characterized by hyper- or hypoinsulinaemia. Hyperinsulinaemia in the basal state usually leads to receptor 'down' regulation as seen in obesity, Type II diabetes, acromegaly, and islet cell tumors. Hypoinsulinaemia such as seen in anorexia nervosa or Type I diabetes may lead to elevated binding.

(2) Disorders involving antireceptor antibodies, which can bind to the receptor and competitively inhibit insulin binding. Such antibodies may act as agonists, antagonists, or partial agonists.

(3) Genetic disorders relating to insulin or the IR.

(4) Disorders of receptor specificity where insulin may bind with different affinity to its own receptor or related receptors such as receptors for insulin-like growth factors.

(5) Disorders of affinity modulation where physical factors such as pH, temperature, ions, and other factors may modify binding to the insulin receptor.

The method and compositions of the invention can be used to treat any of these categories of disorders affecting insulin or the insulin receptor.

Insulin Deficiency or Insulin Resistance Disorders

An IBRA that acts as a agonist of the insulin receptor can be used to treat any disorder associated with insulin deficiency, insulin resistance, insulin receptor deficiency, defective signaling from the insulin receptor, or any combination thereof.

Insulin is a hormone secreted by the pancreas. It helps the body store and utilize blood glucose (blood sugar) by binding with receptors on cells and allowing the glucose to pass from the blood into the cell. Inside the cell, glucose is either used for energy or stored for future use in the form of glycogen in liver or muscle cells.

Insulin resistance refers to a decreased capacity of circulating insulin to regulate glucose uptake and nutrient metabolism. Insulin resistance occurs when the normal amount of insulin secreted by the pancreas is not able bind to the insulin receptor and allows the glucose to pass from the blood into the cell.

Insulin deficiency generally refers to a reduction in the levels of circulating insulin, which can occur, for example, by the autoimmune destruction of pancreatic β-cells that secrete insulin.

Insulin binds to the IR to regulate a number of metabolic and proliferative pathways. As a result, insulin resistance or deficiency can result in a number of disorders described below.

The most well-known disease associated with insulin resistance and deficiency is diabetes. Type I diabetes, or insulin dependent diabetes mellitus (IDDM), is generally associated with insulin deficiency. Although insulin deficiency is the primary defect in IDDM, in patients with poorly controlled IDDM there is also a defect in the ability of target tissues to respond to the administration of insulin. There are multiple biochemical mechanisms that account for this impairment of tissues to respond to insulin. Deficiency in insulin leads to elevated levels of free fatty acids in the plasma as a result of uncontrolled lipolysis in adipose tissue. Free fatty acids suppress glucose metabolism in peripheral tissues such as skeletal muscle. This impairs the action of insulin in these tissues, i.e., the promotion of glucose utilization. Additionally, insulin deficiency decreases the expression of a number of genes necessary for target tissues to respond normally to insulin, such as glucokinase in liver and the GLUT4 class of glucose transporters in adipose tissue. Type II diabetes, is generally associated with insulin resistance but can also be associated with insulin deficiency. Either or both forms of diabetes, and any associated complication of diabetes including, for example, defects in glucose metabolism, lipid metabolism, protein metabolism, diabetic neuropathy, diabetic retinopathy, microvascular and macrovascular diseases, stroke, hypertension, and heart and kidney disease, can be treated with an IBRA (e.g., s-CPG15, s-CPG15-2, or CPG15-2 compounds) that activates insulin receptor signaling.

Insulin levels are also involved in appetite control regulated by the hypothalamus and pituitary glands of the brain that respond to signals indicating high fat stores and hunger. Right after a meal, the amount of glucose in the blood rises and signals the release of insulin, which then pours into the bloodstream. Insulin enables the glucose and amino acids to enter cells in the body, importantly, those in the muscles. Here, insulin and other hormones direct whether these nutrients will be burned for energy or stored for future use. The inability to use insulin efficiently (insulin resistance) or the decrease in insulin production (insulin deficiency) has been associated with both obesity and diabetes.

The hypothalamus is a major integrator of nutritional and hormonal signals. Insulin is a potent anorexigenic hormone that decreases appetite, increases thermogenisis, and increases fat utilization (Menendez et al., *Brain Res.* 555:193-201, 1991; Pliquett et al., *Horm. Metab. Res.* 38:442-446, 2006; Woods et al., *Int. J. Obes.* 14:69-73, 1990). Consistent with the role of insulin in nutritional hypothalamic signaling; insulin receptor is expressed in the hypothalamus and throughout the central nervous system (Pliquett et al., in supra). The IBRAs described herein can be administered to individuals in order to achieve weight loss or appetite suppression.

Insulin deficiency or resistance or impaired signaling from the IR has also been shown to be associated with several neurological conditions including neurodegeneration, Alzheimer's disease, and learning and memory impairment.

Insulin resistance also occurs in hypertension, cardiovascular disease, hyperglycemia, hyperinsulinemia, polycystic ovarian disease, obesity, and dyslipidemia, and metabolic syndrome or syndrome X. The prevalence of insulin resistance is remarkably high, particularly in ageing adult populations (National Diabetes Data Group, "Diabetes in America," National Institutes of Diabetes and Digestive Diseases, National Institutes of Health, U.S.A., 1994), and rising—most rapidly in the young (Mokdad et al., *Diabetes Care* 23:1278-1283, 2000).

The present invention includes the use of an IBRA as an IR agonist for the treatment of any of the disorders, or group of disorders, described above.

Insulin Excess Disorders

An IBRI (e.g., an inhibitor of s-CPG15 or inhibitor of CPG15-2) can be used to treat any disorder associated with excess insulin, excess IR, increased or constitutively active IR, or any combination thereof. Desirably the therapeutic compound is an inhibitor of s-CPG15.

Disorders characterized by hyperinsulinism include insulin and hypoglycemic drug overdose, hypoglycemia, and insulomas. Insulinomas account for about 90% of all pancreatic endocrine tumours. They occur with an incidence of about 0.5 per million population and people of all ages can be affected. These tumors are usually benign but synthesize and secrete insulin autonomously causing spontaneous hypoglycaemia. Symptoms may include deep coma, epilepsy, dizziness, weakness, hunger, and epigastric pain.

Congenital hyperinsulinism is the most common cause of severe, persistent hypoglycaemia in infants. It may be familial, as up to 20% of affected families have more than one affected child. A defect in beta-cell function is the most likely explanation for the hyperinsulinism that can lead to brain damage and death if not detected early.

Gastric dumping syndrome is encountered in approximately 25-50% of patients following gastric surgery and may persist post-operatively for several months. Early dumping usually involves gastrointestinal and vasomotor complaints. Late dumping predominantly involves vasomotor complaints and is a consequence of a reactive hypoglycaemia resulting from hyperinsulinism and an exaggerated release of glucagon-like peptide-1. The gastric dumping syndrome is infrequently reported in children, but is difficult to diagnose and manage, and has significant morbidity.

Neurologic impairment or death often results from conditions of hypoglycemia and hyperinsulinism and therefore, the associated disorders must be managed quickly and effectively. IBRIs, including any inhibitor of s-CPG15 or CPG15-2 (e.g., a inhibitor of s-CPG15-2), or any compound that reduces CPG15 or CPG15-2 expression levels can be used to treat any disorder characterized by excessive insulin or IR levels or biological activity.

IGF-1 or IGF-1R Deficiency or Resistance Disorders

An IBRA (e.g., a s-CPG15, s-CPG15-2, or CPG15-2 compound) can be used to treat any disorder associated with IGF-1 deficiency, IGF-1 resistance, decreased IGF-1 or IGF-1R expression levels or biological activity, or any combination thereof.

IGF-1 is a circulating protein present in high concentrations in the plasma and is detectable in most tissues. IGF-1 stimulates cell differentiation and proliferation and is required by most mammalian cell types for sustained proliferation. IGF-1 is also involved in metabolic regulation pathways and regulates signaling pathways in a manner similar to insulin.

Specific disorders characterized by decreased IGF-1 or IGF-1R levels or biological activity include Type I or Type II diabetes, amyotropic lateral sclerosis, diabetic motor neuropathy (Apfel and Kessler, *CIBA Found. Symp.* 196:98-108, 1996), osteoporosis (Canalis, *Bone* 21:215-216, 1997), immune modulation disorders (Clark, *Endocr. Rev.* 18:157-179, 1997), nephrotic syndrome (Feld and Hirshberg, *Pediatr. Nephrol.* 10:355-358, 1996), amyotrophic lateral sclerosis, osteoporosis, atherosclerosis, smooth muscle restenosis, acromegaly, decreased muscle mass (Rosen et al., *Trends Endocrinol. Metab.* 10:136-141, 1999), and small stature.

IGF-1 or IGF-1R Excess Disorders

An IBRI (e.g., an inhibitor of s-CPG15 or an inhibitor of CPG15-2) can be used to treat any disorder associated with excess IGF-1, excess IGF-1R, increased or constitutively active IGF-1R, or any combination thereof.

A number of studies have shown that IGF-1 can induce cellular proliferation both in vitro and in vivo (Angelloz-Nicoud and Binoux, *Endocrinol.* 136:5485-5492, 1995; Figueroa et al., *J. Clin. Endocrinol. Metab.* 80:3476-3482, 1995; Torring et al., *J. Urol.* 158:222-227, 1997). Additionally, elevated serum IGF-1 levels correlate with increased risks of prostate cancer, and may be an earlier predictor of cancer than is prostate-specific antigen (PSA) (Chan et al., *Science* 279:563-566, 1998). Recent studies have indicated a connection between IGF-1 levels and other cancers including, but not limited to, breast, colorectal, lung, and ovarian.

There is considerable evidence for a role for IGF-I and/or IGF-IR in the maintenance of tumor cells in vitro and in vivo. IGF-IR levels are elevated in tumors of lung (Kaiser et al., *J. Cancer Res. Clin Oncol.* 119:665-668, 1993; Moody et al., *Life Sciences* 52: 1161-1173, 1993; Macauley et al., *Cancer Res.,* 50:2511-2517, 1990), breast (Pollak et al., *Cancer Lett.* 38:223-230, 1987; Foekens et al., *Cancer Res.* 49:7002-7009, 1989; Cullen et al., *Cancer Res.* 49:7002-7009, 1990; Arteaga et al., *J. Clin. Invest.* 84:1418-1423, 1989), prostate and colon (Remaole-Bennet et al., *J. Clin. Endocrinol. Metab.* 75:609-616, 1992; Guo et al., *Gastroenterol.* 102:1101-1108, 1992). Additional examples can be found in U.S. Patent Application Publication No. 20050281812, herein incorporated by reference.

Increased IGF-I levels also correlate with several noncancerous pathological states, including acromegaly and gigantism (Barkan, *Cleveland Clin. J. Med.* 65:343, 347-349, 1998), while abnormal IGF-I/IGF-I receptor function has been implicated in psoriasis (Wraight et al., *Nat. Biotech.* 18:521-526, 2000), atherosclerosis and smooth muscle restenosis of blood vessels following angioplasty (Bayes-Genis et al., *Circ. Res.* 86:125-130, 2000). Increased IGF-I levels also can be a problem in diabetes or in complications thereof, such as microvascular proliferation (Smith et al., *Nat. Med.* 5:1390-1395, 1999).

IGF-1 is also important in the regulation of apoptosis. Apoptosis, which is programmed cell death, is involved in a wide variety of developmental processes, including immune and nervous system maturation. In addition to its role in development, apoptosis also has been implicated as an important cellular safeguard against tumorigenesis (Williams, *Cell* 65:1097-1098, 1991; Lane, *Nature* 362:786-787, 1993). Suppression of the apoptotic program, by a variety of genetic lesions, may contribute to the development and progression of malignancies.

IGF-1 protects from apoptosis induced by cytokine withdrawal in IL-3-dependent hemopoietic cells (Rodriguez-Tarduchy et al., *J. Immunol.* 149:535-540, 1992), and from serum withdrawal in Rat-1/mycER cells (Harrington et al., *EMBO J.* 13:3286-3295, 1994). The protective effects of IGF-1 on apoptosis are dependent upon having IGF-1R present on cells to interact with IGF-1 (Resnicoff et al., *Cancer Res.* 55:3739-3741, 1995). The anti-apoptotic function of IGF-1 is important in the post-commitment stage of the cell cycle and also in cells blocked in cell cycle progression by etoposide or thymidine. The demonstration that c-myc driven fibroblasts are dependent on IGF-1 for their survival suggests that there is an important role for the IGF-1R in the maintenance of tumor cells by specifically inhibiting apoptosis, a role distinct from the proliferative effects of IGF-1 or IGF-1R. This would be similar to a role thought played by other anti-apoptotic genes such as bcl-2 in promoting tumor survival (McDonnell et al., *Cell* 57:79-88, 1989; Hockenberry et al., *Nature* 348:334-336, 1990).

An inhibitor of s-CPG15 or an inhibitor of CPG15-2 that acts as an antagonist of the IGF-1R can be used to treat any disorder characterized by increased IGF-1 or IGF-1R levels or biological activity, as described above, including any of neurological conditions described herein. While IBRAs generally act as agonists of the IR or IGF-1R, and IBRIs act as antagonists of the IR or IGF-1R, it should be noted that the mechanism of action of these molecules can depend on the cell type and may, in some cases, act in an alternative manner. For example, in some cells s-CPG15 may act as a competitive inhibitor of insulin or IGF-1 by binding to and blocking the receptor. Any of the assays for determining activation of the IR or IGF-1R described herein can be used to determine if the tested compound is acting as an agonist or an antagonist in a particular cell type. The tested compound can then be used accordingly for the treatment of the diseases listed above.

Neurological Conditions Associated with Aberrant Insulin or IGF-1 Signaling

Given that CPG15 was originally found to be expressed in a variety of neuronal cells and tissues (e.g., brain, differentiated projection neurons, spinal cord, CNS) and that s-CPG15 was previously shown to act as a survival factor rescuing hippocampal and cortical neurons from cell death, the present invention also features the use of IBRAs to treat or prevent any neurological condition associated with insulin or IGF-1 deficiency or resistance. For example, recent evidence suggests a role for insulin deficiency in the progression of Alzheimer's Disease, neurodegenerative disease (Schubert et al., *J. Neurosci.* 23:7084-7092, 2003) and learning and memory disorders. Studies have shown that diabetic patients are at greater risk of Alzheimer's disease. Additionally, people with schizophrenia are at least twice as likely to develop Type 2 diabetes. In a study of brain samples from 45 Alzheimer's patients, the number of insulin receptors in the frontal cortex, the center of intellect, dropped by 80 percent in advanced cases of the disease, meaning that the cells do not get the insulin they need to survive.

Neurological conditions associated with insulin or IGF-1 excess can be treated using the IBRIs (e.g., inhibitors of s-CPG15 or inhibitors of CPG15-2) described herein. Specific examples of neurological conditions associated with insulin or IGF-1 excess include, but are not limited to, Alzheimer's disease, Parkinson's disease, Huntington's disease, amyotrophic lateral sclerosis (ALS), peripheral neuropathies, stroke, trauma, diabetic neuropathy, appetite control, schizophrenia, neurodegeneration, and learning and memory impairment and other conditions characterized by neuronal death or loss of neurons, whether central, peripheral, or motor neurons.

Combination Therapies

The IBRAs of the invention that are useful as IR or IGF-1R agonists, or IBRIs can be provided in conjunction (e.g., before, during, or after) with additional therapies used to treat or prevent any of the disorders described above. Treatment therapies include but are not limited to insulin or IGF-1 replacement therapy, glucose or dextrose infusion, therapy using hypoglycemic agents, surgery, radiation therapy, chemotherapy, immune therapy, anti-angiogenic therapy, therapies using hypertensive agents, and hormone therapies. If desired, such additional therapies can be combined in a single kit for the treatment of any of the disorders described herein.

Specific examples of human insulin that are commercially available for diabetics, include the fast-acting Humulin™BR and Novolin™, slower acting treatments, such as Protamine-zinc-insulin (PZI), Neutral protamine Hagedorn (NPH) insulin and Lente insulin. Insulin analogues, such as Humalog (LysPro), with altered properties are also available.

Additional examples of blood sugar lowering agents which can be used in combination with the methods and compositions of the invention include GLYNASE™ brand drug (Upjohn) and DIABETA™ brand drug (Hoechst-Roussel). GLUCOTROL™ (Pratt) is the trademark for a glipizide (1-cyclohexyl-3-(p-(2-(5-methylpyrazine carboxamide) ethyl)phenyl)sulfonyl)urea) tablet available in both 5- and 10-mg strengths and is also prescribed to Type II diabetics who require hypoglycemic therapy following dietary control or in patients who have ceased to respond to other sulfonylureas. Additional hypoglycemic agents or drugs affecting insulin action include sulfonylureas, such as the biguanides (e.g., metformin and phenformin) or thiazolidinediones (e.g., troglitozone).

Antisense Nucleobase Oligomers

The present invention features the use of antisense nucleobase oligomers to downregulate expression of cpg15 mRNA or cpg15-2 mRNA which will lead to a reduction in expression of the soluble form of cpg15 or cpg15-2 mRNA or CPG15 or CPG15-2 polypeptides, respectively. The preparation and use of such antisense nucleobase oligomers are described in detail in U.S. Patent Application Publication Nos. 20040176291 and 20050187175, and PCT Publication Nos. WO 2004/031347 and WO 2005/032476, incorporated herein by reference.

RNA Interference

The present invention also features the use of RNA interference (RNAi) to inhibit expression of cpg15 or of cpg15-2 which will lead to a reduction in the expression of s-CPG15 or CPG15-2, respectively. The preparation and use of such RNA interference (RNAi) are described in detail in U.S. Patent Application Publication Nos. 20040176291 and 20050187175 and PCT Publication Nos. WO 2004/031347 and WO 2005/032476, incorporated herein by reference.

Desirably, the antisense nucleobase oligomers or siRNA used for RNA interference will cause an overall decrease preferably of 20% or greater, more preferably of 50% or greater, and most preferably of 75% or greater, in the level of protein or nucleic acid, detected by standard art known assays, as compared to samples not treated with antisense nucleobase oligomers or dsRNA used for RNA interference. Examples of assays for protein expression include western blotting, examples of assays for RNA expression include northern blotting, PCR, and RNase protection assays, and examples of assays for DNA expression include Southern blotting and PCR.

Inhibitory Forms of CPG15

Dominant negative or truncated forms of CPG15 that can inhibit the biological activity, preferably by binding to and blocking activation of the IR or IGF-1R are useful as IBRIs in the methods of the invention. One example is t-CPG15, which lacks the amino acids encoding the GPI linkage sequence (i.e., t-CPG15 includes only amino acids 1-114 or 1-115 of the human CPG15 protein). In general, t-CPG15 is expressed from an engineered construct containing the nucleic acid sequence encoding CPG15 but lacking the nucleotides that encode the GPI linkage sequence. This truncated form of CPG15 does not follow the GPI linkage pathway, but is instead secreted directly out of the cell without membrane attachment or modifications associated with membrane attachment. Details on the truncated form of CPG15 can be found in U.S. Patent Application No. 20040176291 and PCT Publication No. WO 2004/031347. Another example is the dominant negative s-CPG15 shown in FIG. 4B. Dominant negatives are often thought to act by either sequestering a functional form of the protein and rendering it non-functional or by binding to and blocking a receptor for the protein. A candidate truncated or dn-CPG15 can be tested for inhibitory activity using the assays described herein. For example, a dnCPG15 will bind to an IR or IGF-1R but will show less than 90%, 80%, 70%, 60%, 50%, 40%, 30%, 20% or less than 10% of autophosphorylation or substrate phosphorylation of insulin or IGF-1.

Diagnostic Applications

The present invention features methods and compositions for the diagnosis of an insulin deficient or resistant disorder, an insulin excess disorder, an IGF-1 deficient disorder, or an IGF-1 excess disorder, or the propensity to develop any such disorders using CPG15 or CPG15-2 nucleic acid molecules and polypeptides, including polypeptides or nucleic acid molecules that specifically detect the soluble forms of either protein. The methods and compositions can include the measurement of CPG15 or CPG15-2 polypeptides, either free or bound to another molecule, or any fragments or derivatives thereof. Alterations in CPG15 or CPG15-2 expression or biological activity in a test sample as compared to a normal reference can be used to diagnose any of the disorders described herein.

A subject having an insulin deficient or resistant disorder, an insulin excess disorder, an IGF-1 deficient disorder, or an IGF-1 excess disorder, or the propensity to develop any such disorders will show an alteration (e.g., a decrease or increase of 10%, 20%, 30%, 40%, 50%, 60%, 70%, 80%, 90%, or more), in the expression of a CPG15 or CPG15-2 polypeptide or nucleic acid. The CPG15 or CPG15-2 polypeptide can include full-length CPG15 or CPG15-2 polypeptide, degradation products, alternatively spliced isoforms of CPG15 or CPG15-2 polypeptide, enzymatic cleavage products of CPG15 or CPG15-2 polypeptide, and the like. An antibody that specifically binds a CPG15 (including s-CPG15) or CPG15-2 (including s-CPG15-2) polypeptide may be used for the diagnosis of an insulin deficient or resistant disorder, an insulin excess disorder, an IGF-1 deficient disorder, or an IGF-1 excess disorder, or the propensity to develop any such disorders.

Diagnostic methods can include measurement of absolute levels of CPG15 or CPG15-2 or relative levels of CPG15 or CPG15-2, including the soluble forms of either, as compared to a reference sample.

Standard methods may be used to measure levels of CPG15 (including s-CPG15) or CPG15-2 (including s-CPG15-2) polypeptide in any bodily fluid, including, but not limited to, urine, blood, serum, plasma, saliva, amniotic fluid, or cerebrospinal fluid. Such methods include immunoassay, ELISA, western blotting using antibodies directed to CPG15 (including s-CPG15), and quantitative enzyme immunoassay techniques. ELISA assays are the preferred method for measuring levels of CPG15 (including s-CPG15) or CPG15-2 (including s-CPG15-2) polypeptide. Alterations in the levels of CPG15 (including s-CPG15) or CPG15-2 (including s-CPG15-2) polypeptide, as compared to normal controls, are considered a positive indicator of an insulin deficient or resistant disorder, an insulin excess disorder, an IGF-1 deficient disorder, or an IGF-1 excess disorder, or the propensity to develop any such disorder.

The invention also provides for a diagnostic methods and assays test kit for detection of s-CPG15 or biologically active fragment, derivative, or homolog for the diagnosis of any of the insulin or IGF-1 disorders described herein. For example, a diagnostic test kit can include antibodies to s-CPG15 and means for detecting, and more preferably evaluating, binding between the antibodies and s-CPG-15. For detection, the antibody is labeled and substrate-bound, such that the s-CPG15-antibody interaction can be established by determining the amount of label attached to the substrate following binding between the antibody and s-CPG15. A conventional ELISA is a common, art-known method for detecting antibody-substrate interaction and can be provided with the kit of the invention. A kit that determines an alteration in the level of s-CPG15 relative to a reference, such as the level present in a normal control, is useful as a diagnostic kit in the methods of the invention.

Dosages and Therapeutic Uses

By "therapeutically effective dose" herein is meant a dose that produces the therapeutic effects for which it is administered. The exact dose will depend on the condition to be treated, and may be ascertained by one skilled in the art using known techniques. In general, the IBRA, inhibitor of s-CPG15, or inhibitor of CPG15-2 is administered at about 0.01 µg/kg to about 50 mg/kg per day, preferably 0.01 mg/kg to about 30 mg/kg per day, most preferably 0.1 mg/kg to about 20 mg/kg per day. The IBRA may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

A "subject" for the purposes of the present invention includes humans and other animals, preferably warm-blooded mammals including mice, rats, guinea pigs, hamsters, rabbits, cats, dogs, goats, sheep, cows, or monkeys. Thus, the methods are applicable to both human therapy and veterinary applications.

IBRAs or IBRIs of the invention can be administered in a variety of ways, e.g., those routes known for specific indications, including, but not limited to, topically, orally, subcutaneously, intravenously, intracerebrally, intranasally, transdermally, intraperitoneally, intramuscularly, intrapulmonary, vaginally, rectally, intraarterially, intralesionally, intraventricularly in the brain, or intraocularly. IBRAs, inhibitors of s-CPG15, or inhibitors of CPG15-2 (including inhibitors of s-CPG15-2) can be administered continuously by infusion into the fluid reservoirs of the CNS, although bolus injection is acceptable, using techniques well known in the art, such as pumps or implantation. Administration can be accomplished by a constant- or programmable-flow implantable pump or by periodic injections. Sustained release systems can also be used. Generally, where the condition permits, one should formulate and dose the IBRAs or IBRIs of the invention for site-specific delivery. Administration can be continuous or periodic.

Semipermeable, implantable membrane devices are useful as a means for delivering drugs in certain circumstances. For example, cells that secrete s-CPG15 or s-CPG15-2, or inhibitors of s-CPG15 or CPG15-2 can be encapsulated, and such devices can be implanted into a subject, for example, into the brain or spinal cord (CSF) of a subject suffering from Parkinson's Disease. See, U.S. Pat. Nos. 6,042,579; 4,892,538; 5,011,472; 5,106,627; PCT Applications WO 91/10425; 91/10470; Winn et al., *Exper. Neurol.* 113:322-329, 1991; Aebischer et al., *Exper. Neurol.* 111:269-275, 1991; and Tresco et al., *ASAIO* 38:17-23, 1992; each of which is herein incorporated by reference. The pharmaceutical compositions of the present invention comprise IBRAs, inhibitors of s-CPG15, or inhibitors of CPG15-2 (including inhibitors of s-CPG15-2) in a form suitable for administration to a subject. In the preferred embodiment, the pharmaceutical compositions are in a water soluble form, and may include such physiologically acceptable materials as carriers, excipients, stabilizers, buffers, salts, antioxidants, hydrophilic polymers, amino acids, carbohydrates, ionic or nonionic surfactants, and polyethylene or propylene glycol. The IBRAs or IBRIs of the present invention may be in a time-release form for implantation, or may be entrapped in microcapsules using techniques well known in the art. Additional excipients useful for pharmaceutical compositions include any of those listed in U.S. Patent Application No. 20030176672, herein incorporated by reference.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents. Preferred surfactants include Tween 20 and pluronic acid (F68). Suitable surfactant concentrations are 0.005 to 0.02%.

The compositions hereof including lyophilized forms, are prepared in general by compounding the components using generally available pharmaceutical compounding techniques, known per se. Methods well known in the art for making formulations are found, for example, in "*Remington: The Science and Practice of Pharmacy*" ($20^{th}$ ed., ed. A. R. Gennaro, 2000, Lippincott Williams & Wilkins, Philadelphia, Pa.). A particular method for preparing a pharmaceutical composition of IBRAs, inhibitors of s-CPG15, or inhibitors of CPG15-2 (including inhibitors of s-CPG15-2), comprises employing purified (according to any standard protein purification scheme) IBRAs or IBRIs of the present invention in any one of several known buffer exchange methods, such as gel filtration or dialysis.

IBRAs can also be delivered via a nucleic acid encoding cpg15 or cpg15-2 as described in U.S. Patent Application Publication Nos. 20040176291 and 20050187175, and PCT Publication Nos. WO 2004/031347 and WO 2005/032476, herein incorporated by reference.

In Vitro and Ex Vivo Uses

IBRAs can be used in a variety of in vitro applications. Preferably IBRAs are s-CPG15, s-CPG15-2, or CPG15-2 polypeptides, fragments, or derivatives, thereof that bind to and/or activate IR or IGF-1R. These applications include adding s-CPG15 or s-CPG15-2 to cell culture media to promote the growth and survival of cells grown in culture. Purified IBRAs can also be used in stem cell growth applications where both the growth and survival promoting functions as well as the differentiating functions are useful. In addition, purified IBRAs can be used for applications relating to repairing and regenerating damaged tissue or organs by growing the tissue or organs ex vivo in the presence of IBRAs. Such methods are described in detail in U.S. Patent Application Publication Nos. 20040176291 and 20050187175 and PCT Publication Nos. WO 2004/031347 and WO 2005/032476.

Tissue or Organ Transplantation

Purified IBRAs or nucleic acids encoding cpg15 or cpg15-2 can also be used to promote cell survival and/or differentiation for tissue and organ transplantation, the repair of diseased or damaged tissues and organs, and replacement tissue and organ engineering. Preferably IBRAs are s-CPG15, s-CPG15-2, or CPG15-2 polypeptides, fragments, or derivatives, thereof that bind to and/or activate IR or IGF-1R. The survival and differentiation promoting functions of s-CPG15 make this protein amenable as an added nutrient or type of growth factor in methods for sustaining organ or tissue survival in culture, e.g., prior to transplantation of the organ or tissue.

Desirably, the organ is a bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, blood vessel, skin, bone, or cartilage, or any part thereof of these organs. In desired embodiments, the tissue includes one or more cell-types derived from bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, or cartilage.

In addition, a purified IBRA can be used to promote growth and differentiation in applications involving the growth of natural or synthetic tissues or organs in vitro. Such methods are described in detail in U.S. Patent Application Publication Nos. 20040176291 and 20050187175, and PCT Publication Nos. WO 2004/031347 and WO 2005/032476.

Animal Models

The use of animals in medical research is a major way to increase our knowledge of the pathogenesis and alleviation of diseases in both animals and humans. Experiments on animals with induced diseases or conditions can be done under controlled conditions. Mechanisms relating to basic cellular processes such as cell division and apoptosis are highly conserved between species, particularly within mammals. A successful non-human animal model of neuronal cell death offers the prospect of understanding the origin and mechanisms of many neuronal conditions. Existing non-human animal models of neurological conditions can also be used to further explore therapies for neurological conditions. In addition, successful non-human animal models of diabetes, hyperglycemia, and insulin-resistance offer the prospect of further understanding the mechanisms which control insulin-related diseases. Non-human animals can include mice, rats, guinea pigs, hamsters, rabbits, cats, dogs, goats, sheep, cows, monkeys, or other mammals. Animal models can also be used to explore therapies for non-neuronal and non-insulin related conditions. Such methods and use of animal models are described in detail in U.S. Patent Application Publication Nos. 20040176291 and 20050187175, and PCT Publication Nos. WO 2004/031347 and WO 2005/032476.

Screen for Interacting Molecules

While s-CPG15, s-CPG15-2, or CPG15-2, or biologically active fragments, derivatives or homologues thereof, shares little homology to the primary structure of insulin or IGF-1, their requisite secondary structures are similar. The secondary structure of s-CPG15 or s-CPG15-2, especially with respect to the receptor binding domains, can be used to screen for compounds having a similar secondary structure that can be used as IR or IGF-1R agonists or antagonists. Screening assays to detect secondary structure is a useful tool in the high-throughput low-cost screening of candidate compounds. As an example, such a screening method (as described in U.S. Pat. No. 6,875,741, and incorporated herein by reference) can identify additional compounds (synthetic or natural) that bind to IR or IGF-1R and are involved in signaling. Specific compounds can be assayed for IR or IGF-1R agonist or antagonist activity using the methods described herein. Such compounds may be developed as potential therapeutics or as lead compounds to develop other more efficacious ones. In addition, these compounds may be used in high-throughput screens to identify and provide information on small molecules that bind at these sites and mimic or antagonize the functions of insulin or IGF-1. Furthermore, the compounds employed can be used to design secondary peptide libraries, which can be used to identify sequence variants that increase or modulate the binding and/or activity of the original peptide at IR or IGF-1R.

Additional screens using s-CPG15 or s-CPG15-2 that can be used as a screening tool to identify interacting proteins that are important for the induction of cell death pathways are described in U.S. Patent Application Publication Nos. 20040176291 and 20050187175, and PCT Publication Nos. WO 2004/031347 and WO 2005/032476.

EXAMPLES

The features and other details of the invention will now be more particularly described and pointed out in the following examples describing preferred techniques and experimental results. These examples are provided for the purpose of illustrating the invention and should not be construed as limiting.

Example 1 s-CPG15, Insulin, IGF-1, BDNF and NT-3, but not NGF, Protect Cultured Primary Cortical Neurons from Starvation Induced Apoptosis s-CPG15 is able to diffuse between isolated cells and binds membranes of non-CPG15-expressing cells (Putz et al., *Nat. Neurosci.* 8:322-331, 2005). This occurs upon expression of CPG15 in HEK293T and therefore the receptor for s-CPG15 is not restricted to expression in the brain. It must be more ubiquitous. s-CPG15 is also capable of rescuing primary cortical neurons from starvation induced apoptosis (Putz et al., in supra and FIG. 1A). These two observations prompted us to use a dominant negative approach to identify the s-CPG15 receptor. We reasoned that by blocking other growth factors or neurotrophins who have neuroprotective activity with a dominant negative CPG15, the s-CPG15 receptor or the second messenger pathway would be revealed. To do this, we first had to identify factors that are capable of rescuing primary cortical neurons from apoptosis similar to s-CPG15. Insulin and IGF-1 play key roles in neuronal survival (de la Monte and Wands, *J. Alzheimers Dis.* 7:45-61, 2005). The neurotrophin family (BDNF, NT-3, NGF) are also essential for neuronal survival in different neuronal cell types (Barnabe-Heider and Miller, *J. Neurosci.* 23:5149-5160, 2003). Primary cortical neurons undergoing starvation induced apoptosis were incubated with s-CPG15, Insulin (I), Insulin-like growth factor type 1 (IGF-1), brain-derived neurotrophic factor (BDNF, B), neurotrophin-3 (NT-3), and nerve growth factor (NGF) (FIG. 1A). Insulin, IGF-1, BDNF, and NT-3 were able to rescue the neurons from apoptosis similar to s-CPG15. NGF was the only factor tested without a rescue effect.

Example 2

A Dominant Negative Form of CPG15 Inhibits the Survival Effect of Insulin and IGF-1 in Primary Cortical Neurons The deletion of the GPI consensus sequence from the CPG15 cDNA generates a deletion mutant (dnCPG15) (Nedivi et al., *Science* 281:1863-1866, 1998) that still possesses the secretion signal and is therefore secreted into the supernatant of transfected cells, however, no membrane staining of CPG15 expressing and non-expressing cells is observed. In the neuronal starvation assay, dnCPG15 inhibits the ability of wild type CPG15 to rescue neurons from apoptosis (FIG. 1B). We also tested if the co-incubation of dnCPG15 with the previously tested trophic factors, also prevents their ability to rescue neurons from cell death. dnCPG15 prevents insulin and IGF-1 from rescuing neurons undergoing starvation induced apoptosis, while dnCPG15 did not prevent the survival effect of BDNF or NT-3 (FIG. 1B).

Example 3

Inhibition of Insulin Receptor and IGF-1 Receptor Prevent CPG15 Mediated Survival of Primary Cortical Neurons Insulin and IGF-1 function is mediated by the insulin receptor (IR) and the IGF-1 receptor (IGF-1R), which belong to the family of highly homologous tyrosine kinases. To investigate further which of these two receptors is involved in CPG15 signalling, we used specific inhibitors for the insulin and the IGF-1 receptor to see if we could block CPG15 function. The IGF-1 receptor can be blocked by a neutralizing antibody against the IGF-1 receptor that may also weakly cross-react with the insulin receptor (Kull et al., *J. Biol. Chem.* 258:6561-6566, 1983). The kinase activity of the insulin receptor can be specifically blocked by HNMPA, a cell impermeable inhibitor (Baltensperger et al., *Proc. Natl. Acad. Sci. U.S.A.* 89:7885-7889, 1992).

Starving neurons were pre-incubated for 1 hour with the IR-inhibitor HNMPA or the IGF-1 blocking antibody, prior to addition of s-CPG15. In both cases, CPG15 was unable to rescue the neurons from starvation induced apoptosis, implying that s-CPG15 activity is mediated via the IR and IGF-1 receptor (FIG. 2). By blocking either one of the receptors, s-CPG15 rescue function could be completely inhibited. Therefore, this suggests two possible mechanisms through which s-CPG15 can function. First, IGF-1R and IR may be activated to promote s-CPG15 function or alternatively, s-CPG15 binds and acts through a hybrid IR/IGF-1R receptor. Such hybrid receptors are heterodimers from the IR and IGF-1 receptor, which mostly signal IGF-1 activity but can also bind insulin (Bailyes et al., *Biochem. J.* 327:209-215 1997). By using lentivirus delivered RNAi against the IR and the IGF-1R, we knocked down receptor expression in primary cortical neurons. CPG15 was unable to rescue these neurons.

Example 4

Phosphorylation of ERK 1/2 by CPG15

Insulin and IGF-1 share many downstream events in their second messenger signalling pathways. Two main pathways involved in insulin/IGF-1 neuroprotective function are the PI3K/Akt kinase and MAPK pathway. We examined whether CPG15 could phosphorylate ERK1/2, a key protein involved in one of the two pathways.

Primary cortical neurons were incubated with s-CPG15 or insulin (FIGS. 3A and 3B). A Western blot was performed using specific antibodies against phosphorylated ERK1/2. s-CPG15 was able to phosphorylate ERK1/2 to a similar extent as insulin (FIGS. 3A and 3B).

Example 5

The PI3K-Akt Pathway, but not the MAPK Pathway is Necessary for Proper CPG15 Neuronal Survival Function To examine which second messenger pathway/s are involved in CPG15 neuronal rescue function we used specific inhibitors for the PI3K and the ERK1/2 pathway.

Primary cortical neurons undergoing starvation induced apoptosis were incubated with s-CPG15. As shown previously, s-CPG15 alone rescues the neurons from apoptosis. Incubation with the specific PI3K inhibitor LY294002 for 1 hour prior to s-CPG15 treatment, could prevent CPG15 survival function (FIG. 3C).

On the other hand, the specific MEK1 and 2 inhibitor, U0126, was unable to prevent CPG15 induced rescue of apoptotic neurons. In this case, s-CPG15 was able to rescue neurons to the same extent as in the absence of the inhibitor or upon pre-treatment with a negative control for U0126 (U0124). Therefore, this suggests that although s-CPG15 can phosphorylate ERK1/2, the survival function of CPG15 is not through the MAPK pathway, but through the PI3K-Akt pathway.

Materials and Methods.

The following materials and methods were used as cited in the aforementioned Examples 1-5.

Starvation Assay

Primary cortical cultures were grown as described (Putz et al., in supra). Starvation assay was performed as described (Putz et al., in supra), with minor changes. Purified s-CPG15 (50 ng/ml), dominant negative CPG15 (100 ng/ml, dnCPG15), growth factors (insulin, 50 ng/ml (I); insulin-like-growth-factor-1, 50 ng/ml (IGF-1); brain derived neurotrophic factor, 100 ng/ml (BDNF); neurotrophin-3, 50 ng/ml (NT-3); and nerve growth factor, 50 ng/ml (NGF) (all from Sigma)) or inhibitors (insulin receptor inhibitor HNMPA, 200 μM (Sigma); neutralising IGF-1R antibody, 1:100, Ab-1, αIR3 (Calbiochem); PI3K inhibitor LY294002, 50 μM (Biomol); MEK1/2 inhibitor U0126 and U0124, as control (10 μM, Calbiochem); were added as indicated. If factors were used in combination, they were added at the same time. Inhibitors were added 1 h before incubation with growth factors.

ERK1/2 Phosphorylation Assay

Primary cortical neurons were grown in 12 well plates for 6 DIV at a density of $0.75 \times 10^6$. Neurons were washed 3× and starved in MEM (Cambrex) for 2 h. Neurons were incubated with insulin, IGF-1 or CPG15 for 15 min. Neurons were washed with ice-cold DPBS and lysed in 20 μl Laemmli buffer. Western blotting was performed as described (Putz et al., in supra). The Western blot was incubated with an antibody against ERK1/2 or phosphorylated ERK1/2 (1:1000, CellSignaling) in TBS-T, 1% BSA overnight. The second AB was HRP-goat anti rabbit (1:2000, CellSignaling) in TBS-T, 1% milk powder.

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent, or patent application was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of increasing a biological activity of an insulin-binding receptor in an adipocyte, said method comprising contacting said adipocyte with a soluble CPG15 (s-CPG15) comprising a sequence that is at least 95% identical to SEQ ID NO: 1 and having at least one biological activity selected from the group consisting of:
   a) the ability to promote of an adipocyte; and
   b) the ability to promote reduction of of an adipocyte;
wherein said s-CPG15 has the ability to increase an insulin-binding receptor activity.

2. The method of claim 1, wherein said insulin-binding receptor is an insulin receptor or IGF-1 receptor.

3. The method of claim 1, wherein said s-CPG15 consists of the sequence SEQ ID NO: 1.

4. The method of claim 1, wherein said insulin-binding receptor activity is increased by at least 20%.

5. The method of claim 1, wherein said s-CPG15 lacks a signal secretion sequence.

6. The method of claim 1, wherein said s-CPG15 lacks a signal secretion sequence and a GPI linkage sequence.

7. The method of claim 1, wherein said s-CPG15 comprises the sequence of SEQ ID NO: 1.

8. A method of increasing a biological activity of an insulin-binding receptor in an adipocyte, said method comprising contacting said adipocyte with a soluble CPG15 (s-CPG 15) comprising a sequence that is at least 95% identical to SEQ ID NO: 1 and having at least one biological activity selected from the group consisting of:
   a) binding of receptor substrate molecules;
   b) phosphorylation of receptor substrate or downstream molecules;
   c) glucose uptake;
   d) insulin-induced immediate/early gene expression; and
   e) ligand internalization.

* * * * *

UNITED STATES PATENT AND TRADEMARK OFFICE
CERTIFICATE OF CORRECTION

| | | |
|---|---|---|
| PATENT NO. | : 7,884,078 B2 | |
| APPLICATION NO. | : 11/704823 | |
| DATED | : February 8, 2011 | |
| INVENTOR(S) | : Nedivi | |

It is certified that error appears in the above-identified patent and that said Letters Patent is hereby corrected as shown below:

Cover page, under OTHER PUBLICATIONS, in Golen et al., replace
"neuroblastoma, Cell" with --neuroblastoma. Cell--;

Under OTHER PUBLICATIONS, in Golen et al., replace "death and Differentiation" with --Death and Differentiation--;

Under OTHER PUBLICATIONS, in Valverde et al., replace "2003." with --2005.--;

Under OTHER PUBLICATIONS, in Qian et al., replace "TNFalpha" with --TNF alpha--.

Column 5, Line 43, replace "gastic dumping syndrome" with --gastric dumping syndrome--.

Column 10, Line 29, replace "an CPG15-2" with --a CPG15-2--;

Line 35, replace "An CPG15-2" with --A CPG15-2--;

Line 38, replace "an CPG15-2" with --a CPG15-2--.

Column 11, Lines 35-36, replace "s-CPG15-2 mediated" with --s-CPG15-2-mediated--;

Column 11, Line 41, replace "an CPG15-2" with --a CPG15-2--.

Column 12, Line 25, replace "refers to an increase is" with --refers to an increase of--;

Signed and Sealed this
Seventh Day of February, 2012

David J. Kappos
*Director of the United States Patent and Trademark Office*

CERTIFICATE OF CORRECTION (continued)
U.S. Pat. No. 7,884,078 B2

Column 12, Lines 43-44, replace "pancreatic" with --pancreas--.

Column 16, Line 21, replace "or is" with --is--;

Lines 24-25, replace "insulin-like growth factor receptor 1 IGFR 1 and has IGFR 1 biological activity" with --insulin-like growth factor receptor 1 (IGF-1R) and has IGF-1R biological activity--.

Column 17, Lines 43-44, replace "downstream signaling molecules, are known in the art, such as PI3K, ERK, or Akt" with --downstream signaling molecules, such as PI3K, ERK, or Akt--.

Column 21, Line 44, replace "is described" with --are described--.

Column 22, Line 14, replace "and include" with --include--;

Line 29, replace "2d Ed." with --2nd Ed.--.

Column 27, Line 26, replace "phospatidylinositol" with --phosphatidylinositol--;

Lines 32-33, replace "apoptosis, metabolism, gene transcription, proliferation, differentiation, and metabolism" with --apoptosis, gene transcription, proliferation, differentiation, and metabolism--.

Column 30, Line 52, replace "IGF-I" with --IGF-1--;

Line 53, replace "IGF-IR" with --IGF-1R--;

Line 54, replace "IGF-IR" with --IGF-1R--;

Line 66, replace "IGF-I" with --IGF-1--.

Column 31, Line 2, replace "IGF-I/IGF-I receptor" with --IGF-1/IGF-1 receptor--;

Line 6, replace "IGF-I" with --IGF-1--.

Column 36, Line 1, replace "The compositions hereof including lyophilized forms, are" with --The compositions hereof, including lyophilized forms, are--.

CERTIFICATE OF CORRECTION (continued)
U.S. Pat. No. 7,884,078 B2

Column 40, Line 44, replace "CellSignaling" with --Cell Signaling--;

Line 45, replace "CellSignaling" with --Cell Signaling--.

Column 49, Line 21, replace "a) the ability to promote of an adipocyte;" with --a) the ability to promote cell survival of an adipocyte;--;

Line 22, replace "b) the ability to promote reduction of of an adipocyte;" with --b) the ability to promote reduction of cell death of an adipocyte;--.

SEQUENCE LISTING

<160> NUMBER OF SEQ ID NOS: 10

<210> SEQ ID NO 1
<211> LENGTH: 87
<212> TYPE: PRT
<213> ORGANISM: Homo sapiens

<400> SEQUENCE: 1

Ala Gly Lys Cys Asp Ala Val Phe Lys Gly Phe Ser Asp Cys Leu Leu
1               5                   10                  15

Lys Leu Gly Asp Ser Met Ala Asn Tyr Pro Gln Gly Leu Asp Asp Lys
            20                  25                  30

Thr Asn Ile Lys Thr Val Cys Thr Tyr Trp Glu Asp Phe His Ser Cys
        35                  40                  45

Thr Val Thr Ala Leu Thr Asp Cys Gln Glu Gly Ala Lys Asp Met Trp
    50                  55                  60

Asp Lys Leu Arg Lys Glu Ser Lys Asn Leu Asn Ile Gln Gly Ser Leu
65                  70                  75                  80

Phe Glu Leu Cys Gly Ser Gly
                85

<210> SEQ ID NO 2
<211> LENGTH: 165
<212> TYPE: PRT
<213> ORGANISM: Homo sapiens

<400> SEQUENCE: 2

Met Met Arg Cys Cys Arg Arg Cys Cys Cys Arg Gln Pro Pro His
1               5                   10                  15

Ala Leu Arg Pro Leu Leu Leu Pro Leu Val Leu Leu Pro Pro Leu
            20                  25                  30

Ala Ala Ala Ala Ala Gly Pro Asn Arg Cys Asp Thr Ile Tyr Gln Gly
        35                  40                  45

Phe Ala Glu Cys Leu Ile Arg Leu Gly Asp Ser Met Gly Arg Gly Gly
    50                  55                  60

Glu Leu Glu Thr Ile Cys Arg Ser Trp Asn Asp Phe His Ala Cys Ala
65                  70                  75                  80

Ser Gln Val Leu Ser Gly Cys Pro Glu Glu Ala Ala Val Trp Glu
                85                  90                  95

Ser Leu Gln Gln Glu Ala Arg Gln Ala Pro Arg Pro Asn Asn Leu His
            100                 105                 110

Thr Leu Cys Gly Ala Pro Val His Val Arg Glu Arg Gly Thr Gly Ser
        115                 120                 125

Glu Thr Asn Gln Glu Thr Leu Arg Ala Thr Pro Ala Leu Pro Met
    130                 135                 140

Ala Pro Ala Pro Pro Leu Leu Ala Ala Ala Leu Ala Leu Ala Tyr Leu
145                 150                 155                 160

Leu Arg Pro Leu Ala
                165

<210> SEQ ID NO 3
<211> LENGTH: 162
<212> TYPE: PRT
<213> ORGANISM: Mus musculus

<400> SEQUENCE: 3

```
Met Met Cys Asn Cys Cys His Cys His Trp Arg Arg Cys Gln Arg
1               5                   10                  15

Leu Pro Cys Ala Leu Thr Leu Leu Leu Leu Pro Leu Ala Val Ala
                20                  25                  30

Ser Glu Gly Pro Asn Arg Cys Asp Thr Ile Tyr Gln Gly Phe Ala Glu
                35                  40                  45

Cys Leu Ile Arg Leu Gly Asp Gly Met Gly Arg Gly Gly Glu Leu Gln
50                  55                      60

Thr Val Cys Arg Ser Trp Asn Asp Phe His Ala Cys Ala Ser Arg Val
65                  70                  75                  80

Leu Ser Gly Cys Pro Glu Glu Ala Ala Val Trp Glu Ser Leu Gln
                85                  90                  95

Gln Glu Ala Arg Arg Ala Pro His Pro Asp Asn Leu His Ile Leu Cys
                100                 105                 110

Gly Ala Pro Val Ser Val Arg Glu Arg Ile Ala Gly Pro Glu Thr Asn
                115                 120                 125

Gln Glu Thr Leu Arg Ala Thr Ala Pro Ala Leu Ala Pro Ala Pro Ala
                130                 135                 140

Pro Val Leu Leu Ala Ala Ala Leu Ala Leu Ala Cys Leu Leu Gly Pro
145                 150                 155                 160

Leu Ala

<210> SEQ ID NO 4
<211> LENGTH: 142
<212> TYPE: PRT
<213> ORGANISM: Homo sapiens

<400> SEQUENCE: 4

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
                20                  25                  30

Ala Val Phe Lys Gly Phe Ser Asp Cys Leu Leu Lys Leu Gly Asp Ser
                35                  40                  45

Met Ala Asn Tyr Pro Gln Gly Leu Asp Asp Lys Thr Asn Ile Lys Thr
50                  55                      60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
                100                 105                 110

Ser Gly Asn Gly Ala Ala Gly Ser Leu Leu Pro Ala Phe Pro Val Leu
                115                 120                 125

Leu Val Ser Leu Ser Ala Ala Leu Ala Thr Trp Leu Ser Phe
                130                 135                 140

<210> SEQ ID NO 5
<211> LENGTH: 97
<212> TYPE: PRT
<213> ORGANISM: Homo sapien

<400> SEQUENCE: 5

Ala Gly Gly Thr Asp Tyr Lys Asp Asp Asp Lys Cys Asp Ala Val
1               5                   10                  15

Phe Lys Gly Phe Ser Asp Cys Leu Leu Lys Leu Gly Asp Ser Met Ala
```

-continued

```
                20                  25                  30
Asn Tyr Pro Gln Gly Leu Asp Asp Lys Thr Asn Ile Lys Thr Val Cys
         35                  40                  45

Thr Tyr Trp Glu Asp Phe His Ser Cys Thr Val Thr Ala Leu Thr Asp
 50                  55                  60

Cys Gln Glu Gly Ala Lys Asp Met Trp Asp Lys Leu Arg Lys Glu Ser
 65                  70                  75                  80

Lys Asn Leu Asn Ile Gln Gly Ser Leu Phe Glu Leu Cys Gly Ser Gly
                 85                  90                  95

Asn
```

<210> SEQ ID NO 6
<211> LENGTH: 633
<212> TYPE: DNA
<213> ORGANISM: Homo sapiens

<400> SEQUENCE: 6

| | | |
|---|---|---|
| ctcctgcact aggctctcag ccagggatga tgcgctgctg ccgccgccgc tgctgctgcc | 60 |
| ggcaaccacc ccatgccctg aggccgttgc tgttgctgcc cctcgtcctt ttacctcccc | 120 |
| tggcagcagc tgcagcgggc ccaaaccgat gtgacaccat ataccaggc ttcgccgagt | 180 |
| gtctcatccg cttggggga gcatggggcc gcggaggcga gctggagacc atctgcaggt | 240 |
| cttggaatga cttccatgcc tgtgcctctc aggtcctgtc aggctgtccg gaggaggcag | 300 |
| ctgcagtgtg ggaatcacta cagcaagaag ctcgccaggc cccccgtccg aataacttgc | 360 |
| acactctgtg cggtgccccg gtgcatgttc gggagcgcgg cacaggctcc gaaaccaacc | 420 |
| aggagacgct gcgggctaca cgcgcctgca ctccccatggc cctgcgcgcc ccactgctgg | 480 |
| cggctgctct ggctctggcc tacctcctga ggcctctggc ctagcttgtt gggttgggta | 540 |
| gcagcgcccg tacctccagc cctgctctgg cggtggttgt ccaggctctg cagagcgcag | 600 |
| cagggctttt cattaaaggt atttatattt gta | 633 |

<210> SEQ ID NO 7
<211> LENGTH: 608
<212> TYPE: DNA
<213> ORGANISM: Mus musculus

<400> SEQUENCE: 7

| | | |
|---|---|---|
| gacagccagg gatgatgtgc aactgctgcc actgccactg cgccgccgc tgtcagcggc | 60 |
| taccctgtgc cctgacgctg ttgctgctac taccactcgc agtggcctct gagggcccaa | 120 |
| accgctgtga taccatatac caaggctttg ctgaatgtct catccgcctg ggggatggca | 180 |
| tgggtcgagg aggcgagcta cagactgtct gcagatcctg gaatgacttc cacgcctgtg | 240 |
| cctctcgggt cctgtcaggc tgcccagagg aggcggctgc agtgtgggag tcactgcagc | 300 |
| aagaagctcg ccgcgcccca cacccagata atttgcacat cctctgtggc gctcctgtga | 360 |
| gtgttcggga gcggattgct ggcccagaga ccaaccagga cactacggg ccacagctc | 420 |
| ctgcactggc tccagctcca gccctgtgt tgctcgccgc cgctctagcg cttgcctgcc | 480 |
| tcctggggcc tctggcctaa acagtctggt tggccagcca acagtgccct tgcctcccat | 540 |
| cactgcatgc agtggctgcc atgtgagctc tgcagtatgc acacttttca ttaaaggtat | 600 |
| ttatattc | 608 |

<210> SEQ ID NO 8
<211> LENGTH: 104

```
<212> TYPE: PRT
<213> ORGANISM: Mus musculus

<400> SEQUENCE: 8

Ser Glu Gly Pro Asn Arg Cys Asp Thr Ile Tyr Gln Gly Phe Ala Glu
1               5                   10                  15

Cys Leu Ile Arg Leu Gly Asp Gly Met Gly Arg Gly Gly Glu Leu Gln
                20                  25                  30

Thr Val Cys Arg Ser Trp Asn Asp Phe His Ala Cys Ala Ser Arg Val
            35                  40                  45

Leu Ser Gly Cys Pro Glu Glu Ala Ala Ala Val Trp Glu Ser Leu Gln
        50                  55                  60

Gln Glu Ala Arg Arg Ala Pro His Pro Asp Asn Leu His Ile Leu Cys
65                  70                  75                  80

Gly Ala Pro Val Ser Val Arg Glu Arg Ile Ala Gly Pro Glu Thr Asn
                85                  90                  95

Gln Glu Thr Leu Arg Ala Thr Ala
            100

<210> SEQ ID NO 9
<211> LENGTH: 104
<212> TYPE: PRT
<213> ORGANISM: Homo sapiens

<400> SEQUENCE: 9

Ala Ala Gly Pro Asn Arg Cys Asp Thr Ile Tyr Gln Gly Phe Ala Glu
1               5                   10                  15

Cys Leu Ile Arg Leu Gly Asp Ser Met Gly Arg Gly Gly Glu Leu Glu
                20                  25                  30

Thr Ile Cys Arg Ser Trp Asn Asp Phe His Ala Cys Ala Ser Gln Val
            35                  40                  45

Leu Ser Gly Cys Pro Glu Glu Ala Ala Ala Val Trp Glu Ser Leu Gln
        50                  55                  60

Gln Glu Ala Arg Gln Ala Pro Arg Pro Asn Asn Leu His Thr Leu Cys
65                  70                  75                  80

Gly Ala Pro Val His Val Arg Glu Arg Gly Thr Gly Ser Glu Thr Asn
                85                  90                  95

Gln Glu Thr Leu Arg Ala Thr Ala
            100

<210> SEQ ID NO 10
<211> LENGTH: 142
<212> TYPE: PRT
<213> ORGANISM: Mus musculus

<400> SEQUENCE: 10

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
                20                  25                  30

Ala Val Phe Lys Gly Phe Ser Asp Cys Leu Leu Lys Leu Gly Asp Ser
            35                  40                  45

Met Ala Asn Tyr Pro Gln Gly Leu Asp Asp Lys Thr Asn Ile Lys Thr
        50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
```

```
                        85                  90                  95
Glu Ser Lys Asn Leu Asn Ile Gln Gly Ser Leu Phe Glu Leu Cys Gly
            100                 105                 110

Ser Ser Asn Gly Ala Ala Gly Ser Leu Leu Pro Ala Leu Ser Val Leu
        115                 120                 125

Leu Val Ser Leu Ser Ala Ala Leu Ala Thr Trp Phe Ser Phe
    130                 135                 140
```